United States Patent
Gorman et al.

(10) Patent No.: US 11,282,609 B1
(45) Date of Patent: Mar. 22, 2022

(54) MODULAR DATA SYSTEM FOR PROCESSING MULTIMODAL DATA AND ENABLING PARALLEL RECOMMENDATION SYSTEM PROCESSING

(71) Applicant: Chorus Health Inc., San Francisco, CA (US)

(72) Inventors: Scott Gorman, Oakland, CA (US); Arfa Rehman, San Francisco, CA (US)

(73) Assignee: Chorus Health Inc., San Francisco, CA (US)

( * ) Notice: Subject to any disclaimer, the term of this patent is extended or adjusted under 35 U.S.C. 154(b) by 0 days.

(21) Appl. No.: 17/346,290

(22) Filed: Jun. 13, 2021

(51) Int. Cl.
| | |
|---|---|
| G16H 50/20 | (2018.01) |
| G16H 50/30 | (2018.01) |
| G06N 7/00 | (2006.01) |
| G16B 20/00 | (2019.01) |
| G16H 20/00 | (2018.01) |
| G06N 20/10 | (2019.01) |

(52) U.S. Cl.
CPC ............ *G16H 50/20* (2018.01); *G06N 7/005* (2013.01); *G06N 20/10* (2019.01); *G16B 20/00* (2019.02); *G16H 20/00* (2018.01); *G16H 50/30* (2018.01)

(58) Field of Classification Search
CPC ........ G16H 10/00–80/00; G06N 3/00–99/007; G16B 5/00–99/00
See application file for complete search history.

(56) References Cited

U.S. PATENT DOCUMENTS

| | | | | |
|---|---|---|---|---|
| 11,109,083 | B2 * | 8/2021 | Saini | G06N 20/20 |
| 2018/0158552 | A1 * | 6/2018 | Liu | G06N 3/0445 |
| 2020/0051679 | A1 * | 2/2020 | Bostic | G16H 50/30 |

(Continued)

FOREIGN PATENT DOCUMENTS

| | | | | |
|---|---|---|---|---|
| CA | 3088204 A1 * | 7/2019 | | G06N 3/0454 |
| RU | 2703679 C2 * | 10/2019 | | G16H 10/60 |

(Continued)

OTHER PUBLICATIONS

Esteva et al., "A guide to deep learning in healthcare," Nature Medicine | vol. 25 24 | Jan. 2019 | 24-29. (Year: 2019).*

(Continued)

*Primary Examiner* — Elaine Gort
*Assistant Examiner* — Jonathon A. Szumny
(74) *Attorney, Agent, or Firm* — Shah IP Law, PLLC

(57) ABSTRACT

The present invention(s) provide systems and methods for identifying one or more long-term health conditions that a patient may be suffering from, and providing an appropriate intervention plan for managing the health condition. In addition, the present invention(s) provide systems and methods for prioritizing among various potential long-term health conditions that a patient may suffer from, and provide an appropriately prioritized intervention plan for managing a variety of health conditions. Finally, the present invention(s) provide systems and methods for continuously monitoring patient health and/or outcome data to appropriately change an intervention plan based on the specific response that may be exhibited by a patient. In this manner the present invention(s) provide a systematized approach for managing long-term health conditions that previously required guesswork and continuous trial and error.

18 Claims, 9 Drawing Sheets

(56) References Cited

U.S. PATENT DOCUMENTS

| | | | | |
|---|---|---|---|---|
| 2020/0311556 | A1* | 10/2020 | Francon | G06N 3/0454 |
| 2020/0342958 | A1* | 10/2020 | McGovern | C12Q 1/6883 |
| 2020/0356834 | A1* | 11/2020 | Zhou | G06F 1/324 |
| 2020/0365238 | A1* | 11/2020 | Kazemi Oskooei | G06N 3/0454 |
| 2020/0373017 | A1* | 11/2020 | Wang | G16H 50/20 |
| 2021/0057071 | A1* | 2/2021 | Barber | G16H 50/20 |
| 2021/0134430 | A1* | 5/2021 | Mason | G07F 17/0092 |
| 2021/0142904 | A1* | 5/2021 | Michuda | G16B 20/20 |
| 2021/0202103 | A1* | 7/2021 | Bostic | G16H 50/30 |
| 2021/0233662 | A1* | 7/2021 | Sun | G06N 7/005 |

FOREIGN PATENT DOCUMENTS

| | | | | |
|---|---|---|---|---|
| WO | WO-2017136799 | A1 * | 8/2017 | G16H 40/63 |
| WO | WO-2018192672 | A1 * | 10/2018 | G06N 3/0454 |
| WO | WO-2021101934 | A1 * | 5/2021 | H04N 21/6112 |

OTHER PUBLICATIONS

Rao et al., "Deep Learning of Markov Model-Based Machines for Determination of Better Treatment Option Decisions for Infertile Women," Reproductive Sciences (2020) 27:763-770. (Year: 2020).*
Li et al., "Inferring multimodal latent topics from electronic health records," Nature Communications | (2020) 11:2536 (Year: 2020).*
Aamodt et al., Case-Based Reasoning: Foundational Issues, Methodological Variations, and System Approaches, Aug. 2001; 28 pages.
Aliferis et al., Causal Explorer User's Manual, Department of Biomedical Informatics, Vanderbilt University; 26 pages.
Chorus Health System Description; 17 pages.
Elinas et al., Variational Inference for Graph Convolutional Networks in the Absence of Graph Data and Adversarial Settings, Oct. 10, 2020; 24 pages.
GitHub—cyoon1729/deep-Q-networks: Implementations of algorithms from the Q-learning family, Jul. 7, 2021; 2 pages.
Jonnalagadda Venkata Krishna, Sparse, Stacked and Variational Autoencoder; Dec. 6, 2018; 15 pages.
Kiragu et al., Case based Reasoning for Treatment and Management of Diabetes, International Journal of Computer Applications, vol. 145—No. 4, Jul. 2016; 10 pages.
Loftus et al., Decision Analysis and Reinforcement Learning in Surgical Decision-Making, Author manuscript, Aug. 2020; 27 pages.
Ribas et al., Severe sepsis mortality prediction with logistic regression over latent factors, Jul. 19, 2010; 22 pages.
Mctor et al., Key figure impact in trust-enhanced recommender systems, Ai Communications, Jan. 2008; 18 pages.
Wang et al., Dueling Network Architectures for Deep Reinforcement Learning, Apr. 5, 2016; 15 pages.

* cited by examiner

MODULAR DATA SYSTEM FOR PROCESSING MULTIMODAL DATA AND ENABLING PARALLEL RECOMMENDATION SYSTEM PROCESSING

CROSS-REFERENCE TO RELATED APPLICATIONS

None.

BACKGROUND

Field of Art

The present invention(s) is for modular machine learning (ML) data processing systems and methods. More specifically, the present inventions provide systems and methods for processing multimodal and/or a multilevel data with a system architecture for providing fall back recommendations.

Background

In certain ML and artificial intelligence (AI) systems, deep reinforcement learning (DRL) techniques are often preferred. DRL combines artificial neural networks with a reinforcement learning architecture that enables software-defined agents to learn the best actions possible in a virtual environment in order to attain their goals. That is, it unites function approximation and target optimization, mapping state-action pairs to expected rewards. However, in certain circumstances, such as the ones described here, for example, the underlying mechanisms for state-action pairs are not well understood, and there are no actionable models that could be implemented. In such circumstances, DRL could have some disadvantages.

In such cases, some have proposed using dueling network architectures based on the Dueling Q-Network (DQN). This architecture is particularly well suited for model-free RL because, for instance, this architecture explicitly separates the representation of state values and (state-dependent) action advantages. The DQN consists of two streams that represent the value (e.g. quality of an intervention) and advantage functions (e.g. proposing a given therapeutic approach), while sharing a common feature learning module.

DQNs typically use a convolutional neural network (CNN) learning model. CNNs tend to perform well when new data is similar to the training data. However, slight variation in the way that new data may be presented may cause the CNN to perform poorly. The typical way to deal with this variation problem is to use data augmentation techniques. For example, data augmentation techniques provide for presenting the same underlying data in a variety of different ways to improve the CNN's performance. However, in certain circumstances, such as the ones describe below, data augmentation techniques are unavailable because they can lead to classification mistakes and/or may be undesired. In such case, data scientist are unable to deal with certain data and certain classification problems effectively.

Moreover, DQNs also have their own disadvantages that are separate from the CNN problem described above. DQNs can require significant compute capabilities as it requires separate neural networks to be trained to calculate the function estimator. Moreover, the estimator is not trained based on ground-truth data and relies on its own estimation to train itself, which can be problematic in certain fields, such as the ones described below. In addition, there is no guarantee that the model will converge. As such, data scientists often struggle with implementing DQNs in certain cases, including, but not limited to, the cases described below.

Some exemplary cases where DQN and CNN techniques fall short, include certain long-term health conditions, such as menopause, autoimmune disorders, chronic pain associated with physiological and psychological stress, nutritional deficiencies, irritable bowel syndrome, etc. are prevalent across various patient populations. However, they are difficult to treat because they typically present multiple physical and mental symptoms that change and evolve over months and/or years. For example, menopause has more than 50 symptoms that are clinically associated with the condition. Several autoimmune conditions present over 10-20 symptoms. Moreover, these symptoms vary from patient to patient, which can make them especially difficult to identify or diagnose. The problem can be severely exacerbated in patients that have multiple long-term health conditions. As such, the sheer volume and variability in symptoms associated with certain long-term health conditions makes it nearly impossible for patients and/or providers to accurately diagnose and/or identify the relevant conditions in a reasonable amount of time.

Once a diagnosis is made, identifying appropriate intervention techniques for dealing with these long-term health conditions can be equally, if not more, difficult. Generally, there is no single treatment or a "cure" for these conditions. And, patients and doctors rarely know which intervention pathway is going to be effective. As such, patients and medical providers have essentially shifted to treatment regimes to "manage" these conditions. In some instances, these types of long-term health conditions can be effectively managed by behavioral and/or medical interventions. However, the specific intervention that may be required is not always clearly apparent. Compounding the problem, different treatments or approaches may prove to be effective in one patient and not the other even if both patients are suffering from the same long-term health conditions. Indeed, it is not uncommon for patients and providers to spend years in trial and error in an effort to find the right combination of interventions that are effective at managing these conditions. This process unduly increases the time before a patient's symptoms may be alleviated. Moreover, this approach can lead to prematurely applying high-risk or risk-prone medicinal and/or behavioral interventions, which can lead to adverse outcomes. In any event, the sheer number of potential interventions and the variability in their effectiveness makes it very difficult for patients and/or providers to treat the relevant conditions in an effective manner and within a reasonable amount of time.

Indeed, currently, because of the complexity and variability associated with these conditions, patients and/or providers who are battling these conditions are left to "guess" the specific cause of their physical and/or mental symptoms, and "guess" an effective intervention plan that would help them manage these conditions.

SUMMARY

The present inventions provide systems and methods for overcoming the issues described above with regards to DQNs and CNNs, and provides a novel data architecture for processing data such as the long-term health conditions described herein. More specifically, the present invention discloses using stacked autoencoders (including, but not limited to variational autoencoders) with a DQN. The stacked autoencoders are better suited for certain problems because they provide an embedding of the data available (i.e. knowledge representation). Autoencoders in general such as stacked autoencoders, restricted Boltzmann Machines and, in particular, variational autoencoders are particularly well-suited for the problem at hand because they both summarize the knowledge/information available in the data and when properly regularized in training, they allow the generation of new data, which is particularly useful for estimating the posterior probability of certain states (variational inference in statistics). Thus, the training process of the DQN is optimized. This estimation of posterior probabilities is very important to ascertain risk of exacerbations in healthcare applications, such as the ones described below. Indeed, not only does this summary represent the state of the art at a given time but also allow the assessment of the probability to transition to other states so that recommendations and interventions can be planned to maximize this transition probability to the most favorable state for the patient.

In addition, the present inventions provide systems and methods for working with DQNs more generally. As described above, a disadvantage of DQNs is that they are not trained based on ground-truth data and there is no guarantee that the model will converge. The present disclosure overcomes these limitations by using a modular data processing system that applies three different recommendation systems (a deep reinforcement learning technique (hereinafter "DRL") and a dueling network architecture (hereinafter "DQN"), which, together, is also referred to as "DRL-DQN," a reinforcement learning technique ("RL"), and a case-based-reasoning technique "CBR") to the same set of harmonized data to make intervention recommendations.

To accommodate a multi-system recommendation approach, the present systems and/or methods are comprised of a modular data and analysis pipeline, which is an innovation in this space. In one instance, the underlying data may be multi-modal such as text (eg. diagnosis and symptoms), physiologic data (heart-rate, blood pressure and tests—genetic or hormonal), wearable/sensor/smartphone data (e.g. (physical activity or sleep data) and/or multilevel data (i.e. data ranges from physiologic levels to life-style or psychology). All of this data is phenotyped using machine learning techniques for modular and flexible analysis. In this manner, because the underlying data is connected to patient outcomes, new factors may be added that are considered relevant in the management of long-term conditions or discard others that become irrelevant. As such, the models developed for each condition can be optimized and adapted to the evolution of each phenotype (or patient) as new data becomes available. Additionally, this modularity makes the inventive models and infrastructure compatible with data from different repositories (public and private), thus enabling the integration of results coming from different clinical studies.

These systems and/or methods are further enhanced by the inclusion of a CBR methodology, which enables semi-supervised training (i.e. the system is trained only on the most relevant data and outcomes) of the different recommendation engines with the most relevant patient phenotypes and trajectories. Thus, all modules and models will be personalized from their very first release.

Finally, the concurrence and/or integration of CBR with DRL-DQN is another innovation of the presently disclosed systems and/or methods. With this approach, DRL-DQN is used as the learning algorithm for extracting the most relevant cases from the knowledge base and also adapt the proposed interventions for a new case. This system is also trained in a semi-supervised manner. In other words, in one embodiment, CBR techniques may be used for case extraction and DRL-DQN as a recommendation system. In another embodiment, DRL-DQN techniques may be used for knowledge extraction and recommendation in CBR to implement the whole modular system.

In accordance with a specific application or embodiment, the present invention(s) provide systems and methods for identifying one or more long-term health conditions that a patient may be suffering from, and providing an appropriate intervention plan for managing the health condition. In addition, the present invention(s) provide systems and methods for prioritizing among various potential long-term health conditions that a patient may suffer from, and provide an appropriately prioritized intervention plan for managing a variety of health conditions. Finally, the present invention(s) provide systems and methods for continuously monitoring patient health and/or outcome data to appropriately change an intervention plan based on the specific response that may be exhibited by a patient. In this manner the present invention(s) provide a systematized approach for managing long-term health conditions that previously required guesswork and continuous trial and error.

More specifically, the present invention(s) may be embodied as an integrated, full-stack health system for managing and alleviating symptoms of long-term health conditions by utilizing a combination of behavioral interventions and medical interventions to maximize efficacy and impact on health outcomes. The systems and methods begin by employing artificial intelligence to analyze a user's medical history combined with a database of treatments and real-time mobile health tracking capabilities for symptoms, physical activities, lifestyle characteristics, etc. The systems and methods then utilize this data to generate a personalized, and continuously updated, regimen of digitally delivered and research-backed behavioral treatments, such as cognitive behavioral therapy (CBT), mindfulness-based stress reduction (MBSR), as well as personalized recommendations for over the counter and prescription treatments. These systems and methods operate according to health protocols developed in consultation with medical experts and clinical research. It maximizes long-term health benefits and minimizes potentially negative side-effects by first prescribing behavior and lifestyle modifications before progressing to recommendations for more invasive and risk-prone options such as prescription medicines. Throughout the process user health data is collected and used to continuously adapt recommendations according to symptom presentation in a positive feedback loop. In addition, the systems and methods also use machine learning to predict the efficacy of particular treatments for individual patients based on aggregate data collected on cohorts of patients.

BRIEF DESCRIPTION OF THE DRAWING FIGURES

The accompanying drawings illustrate several embodiments and, together with the description, serve to explain the principles of the invention according to the embodiments. It will be appreciated by one skilled in the art that the particular arrangements illustrated in the drawings are merely exemplary and are not to be considered as limiting of the scope of the invention or the claims herein in any way.

DETAILED DESCRIPTION OF EMBODIMENTS

Figure 1:
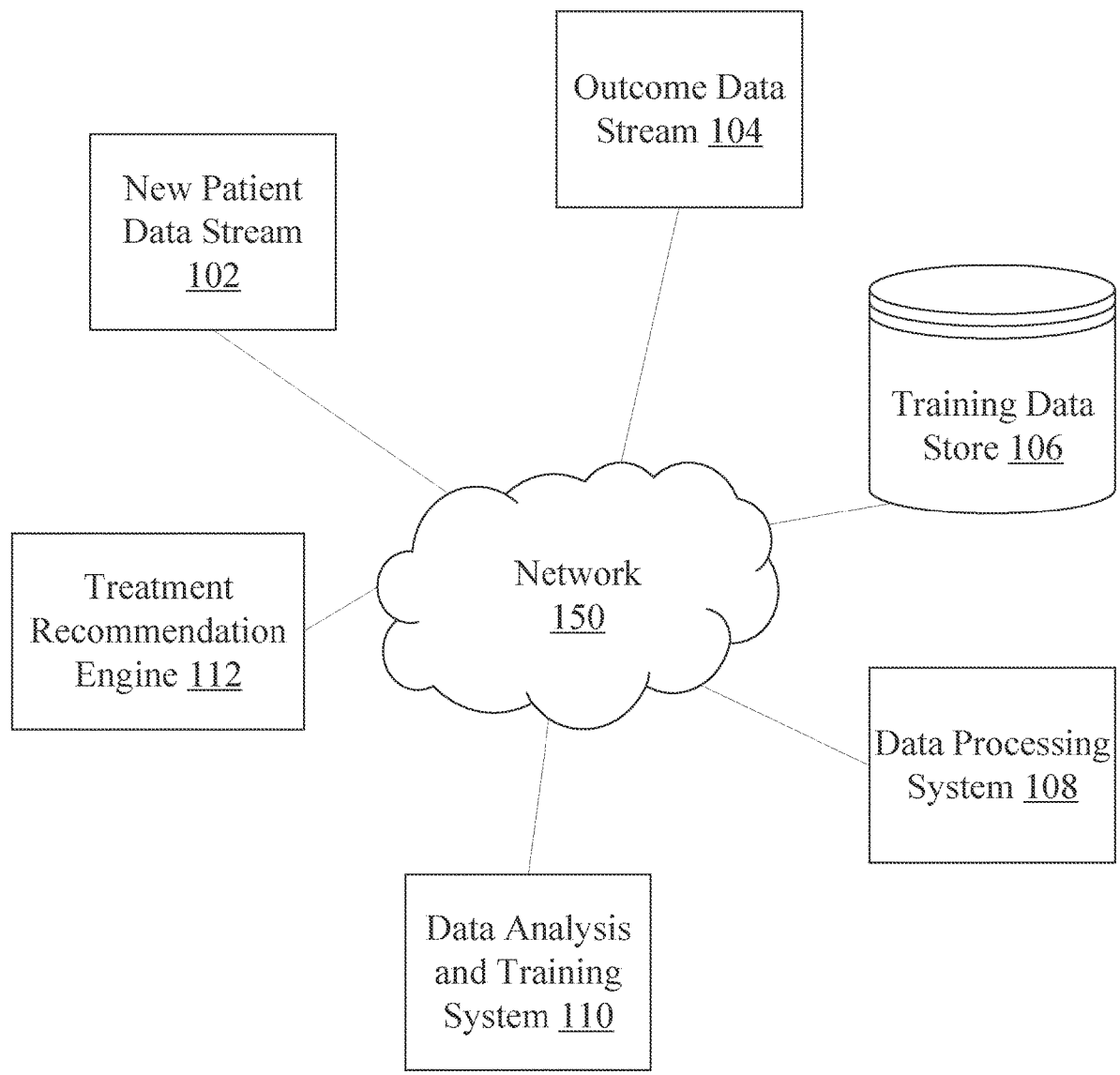
FIG. 1 illustrates a cloud environment used to implement an exemplary AI based training and recommendation system, in accordance with an embodiment of the invention.

The inventive system and method (hereinafter sometimes referred to more simply as "system" or "method") described herein provides a treatment recommendation engine for clinicians to create personalized intervention plans and keep track of patients' progress for these plans, including the detection of possible abnormalities of patient behavior during duration of the plan and the creation of adaptations to the initial plans to correct for detected deviations.

One or more different embodiments may be described in the present application. Further, for one or more of the embodiments described herein, numerous alternative arrangements may be described; it should be appreciated that these are presented for illustrative purposes only and are not limiting of the embodiments contained herein or the claims presented herein in any way. One or more of the arrangements may be widely applicable to numerous embodiments, as may be readily apparent from the disclosure. In general, arrangements are described in sufficient detail to enable those skilled in the art to practice one or more of the embodiments, and it should be appreciated that other arrangements may be utilized and that structural, logical, software, electrical and other changes may be made without departing from the scope of the embodiments. Particular features of one or more of the embodiments described herein may be described with reference to one or more particular embodiments or figures that form a part of the present disclosure, and in which are shown, by way of illustration, specific arrangements of one or more of the aspects. It should be appreciated, however, that such features are not limited to usage in the one or more particular embodiments or figures with reference to which they are described. The present disclosure is neither a literal description of all arrangements of one or more of the embodiments nor a listing of features of one or more of the embodiments that must be present in all arrangements.

Headings of sections provided in this patent application and the title of this patent application are for convenience only and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an aspect with several components in communication with each other does not imply that all such components are required. To the contrary, a variety of optional components may be described to illustrate a wide variety of possible embodiments and in order to more fully illustrate one or more embodiments. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the embodiments, and does not imply that the illustrated process is preferred. Also, steps are generally described once per aspect, but this does not mean they must occur once, or that they may only occur once each time a process, method, or algorithm is carried out or executed. Some steps may be omitted in some embodiments or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other embodiments need not include the device itself.

Techniques and mechanisms described or referenced herein will sometimes be described in singular form for clarity. However, it should be appreciated that particular embodiments may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of various embodiments in which, for example, functions may be executed out of order from that shown or discussed, including substantially concurrently or in reverse order, depending on the functionality involved, as would be understood by those having ordinary skill in the art.

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well known structures and components are shown in block diagram form in order to avoid obscuring such concepts.

FIG. 1 illustrates a high-level architectural view of the invention, in accordance with an embodiment of the invention. The system may be implemented in cloud architecture using, for example, Python with Jupyter notebooks in a cloud platform such as Amazon EMR. This cloud-based architecture permits a capability to ingest, harmonize, store, and analyze large amounts of data from multiple data sources. The system may also be implemented in other databases and/or servers, including on-premises systems, etc. As illustrated, the system may be comprised of a training data store 106, a data processing system 108, a data analysis and training system 110, a treatment recommendation engine 112, new patient data stream 102, and outcome data stream 104. However, the system may be implemented differently as would be readily apparent to a person of ordinary skill in the art.

The raw data streams represent data obtained and/or obtainable from a variety of different sources. In one embodiment, the data ingestion from the raw data streams may start with the connection to the different data sources through API connections and the raw data may be stored in a cloud-based database. In other embodiments, the data may be obtained via other techniques that may be known to a person of ordinary skill in the art, including but not limited to, data scrapes, screen crapes, etc. The raw data stream may represent patient symptom data, health data.

The data processing system 108 incorporates various processing engines used to ingest, harmonize, and homogenize input data that is received from the training data store 106 and/or from any number of data sources. In one embodiment, the data processing system 108 establishes data taxonomies to provide a unified view of the data, introduces common terminologies and semantics across the multiple data sources. The taxonomies establish a hierarchy within a set of metadata and segregating it into different categories (e.g. health data, life-style data, pharmacological treatments, non-pharmacological treatments, supplements, and so on) to create a better understanding of the relationships between data points. In an exemplary embodiment, sensitive health data is processed according to privacy and security standards. The data processing system 108 explores the data for compliance with the established taxonomy, and aggregates it into a single repository (such as training data store 106, described below in great detail) following the predefined data taxonomy, annotated and harmonized into a cohesive cloud database (such as training data store 106). Taxonomy compliance can be assessed by the data processing system 108 by checking the presence of all attributes/variables, their correspondence with their corresponding level category and their measures or names (for text values) corresponding to a predefined format. Moreover, it is this taxonomy validation that performs the checking for aberrant values (e.g. a 1000 Kg person or a pain scale of 20 when the maximum should be 10). These aberrant values shall be annotated for a posterior manual assessment (and fixing) or just censoring of these values during the training phase. In one embodiment, the processed data is stored in a harmonized training data store database 106. In one embodiment, these operations can be performed in Python with Jupyter notebooks in a cloud platform for big data processing such as Amazon EMR®. The data repository infrastructure can be connected to the analysis infrastructure through a proxy connection and the necessary datasets for each condition can be accessed through a standard search engine such as elasticsearch. The analysis platform can be implemented through an analysis service such as Sagemaker®.

The training data store 106 may store the data that has been processed by the data processing system 108. For example, the previously ingested, harmonized, homogenized, and processed data may be used for training and validating various AI (Artificial Intelligence) engines incorporated in the system and described in greater detail below.

The data analysis and training system 110 incorporates various engines that selectively set up and provide training for different ML (Machine Learning) modules, including an RL (reinforcement learning) training engine, a CBR (case-based reasoning) engine, and engines related to training DRL (deep reinforcement learning) and DQN (dueling q-network) learning models. The data analysis and training system 110 is described in greater detail in reference to FIG. 3, however, generally, it performs knowledge extraction steps of ascertaining patient phenotypes from available patient symptom and health data. This phenotyping can be done through unsupervised consensus k-means clustering or through standard multivariate methods such as factor analysis. The methods may optionally be implemented in the scikit-learn library in Python. Moreover, in accordance with an embodiment of the invention, the data analysis and training system 110 may ascertain associations between phenotypes and the available treatments with the objective of obtaining patient trajectories. In essence, the association analysis unveils relationships between phenotypes (and their corresponding attributes) and treatments over time. Associations are typically assessed through correlations or mutual information between phenotypes. With this approach, the data analysis and training system 110 obtains an informative subset of data consisting of phenotypes (including their corresponding attributes) and the most informative treatments at a given point of time. This association analysis can be performed with, for example, the causal explorer package, which assesses mutual information between attributes for the association analysis.

The treatment recommendation engine 112 applies the trained models to incoming data streams to provide treatment or intervention recommendations. In one embodiment, the treatment recommendation engine 112 applies the models trained by the data analysis and training system 110. For example, the treatment recommendation engine 112 applies a trained RL engine, a trained DRL-DQN engine, or a CBR engine to incoming data streams, including, but not limited to, new patient data 102 and outcome data stream 104 (which, for example, may provide new data about how a patient is responding to a previously prescribed interventions).

The modular aspect of the data analysis and training system 110, and treatment recommendation engine 112 (in training and/or applying one or more ML models in parallel and/or serially) highlights additional novel aspects of the inventions described herein. For example, the modular implementation of the treatment recommendation engine 112 allows two actionable fall-back plans in the event of failing to obtain actionable results with the DQN. The first plan includes falling back to a standard RL approach taking the association analysis as a building block for the definition of a Markov Decision Process (MDP). For the case that the association analysis yields unmanageable results, it is possible to take the attributes (phenotypes) that are most closely related to the treatments and outcomes and build a case-based-reasoning (CBR) AI module with probabilistic clustering so that the most similar and successful cases are presented as the best approach. These two fall-back plans only require changing the DRL training module and the DRL recommendation engine for a standard RL training and recommendation modules or the retrieval module for CBR. Moreover, the two fall-back plans also enable the incremental development of the platform and obtain two good baseline recommenders for the system against which the new DQN-DRL can be compared with.

New patient data stream 102 refers to new data associated with a patient who may be suffering from long-term health conditions. It may include, but is not limited to, symptom information that the patient is suffering from. Additional details may include data regarding the severity, frequency, etc., which may help identify patient phenotypes. In one embodiment, new patient data 104 may be obtained from a number of data sources, including information from diagnostics, lifestyle, activity, and so on. The new patient data 102 can be complex, as including, for example, numeric values, text, monitoring data, etc. Sources of new patient data 102 might include, for example, responses made by the patient from a standard questionnaire or physiologic data such as heart rate, blood pressure and genetic or hormonal test results, data on physical activity or sleep from wearable/sensor/smartphone data and multilevel data from physiologic levels to life-style or psychology.

The outcome stream 104 refers to data obtained after an intervention plan or protocol is recommended to and/or implemented by a patient. It refers to data regarding adherence to the recommended protocol, symptom data, psychosocial metrics data, and quality of life metrics data that can be monitored. Outcome data 104 may be obtained from a number of data sources, including information from diagnostics, lifestyle, activity, and so on. The outcome data 104 can be complex, as including, for example, numeric values, text, monitoring data, etc. Sources of outcome data for a new patient might include, for example, responses made by the patient from a standard questionnaire or physiologic data such as heart rate, blood pressure and genetic or hormonal test results, data on physical activity or sleep from wearable/sensor/smartphone data and multilevel data from physiologic levels to life-style or psychology.

Network cloud 150 generally represents a network or collection of networks (such as the Internet or a corporate intranet, or a combination of both) over which the various components illustrated in FIG. 1 (including other components that may be necessary to execute the system described herein, as would be readily understood to a person of ordinary skill in the art). In particular embodiments, network 150 is an intranet, an extranet, a virtual private network (VPN), a local area network (LAN), a wireless LAN (WLAN), a wide area network (WAN), a metropolitan area network (MAN), a portion of the Internet, or another network 150 or a combination of two or more such networks 150. One or more links connect the systems and databases described herein to the network 150. In particular embodiments, one or more links each includes one or more wired, wireless, or optical links. In particular embodiments, one or more links each includes an intranet, an extranet, a VPN, a LAN, a WLAN, a WAN, a MAN, a portion of the Internet, or another link or a combination of two or more such links. The present disclosure contemplates any suitable network 150, and any suitable link for connecting the various systems and databases described herein.

The network 150 connects the various systems and computing devices described or referenced herein. In particular embodiments, network 150 is an intranet, an extranet, a virtual private network (VPN), a local area network (LAN), a wireless LAN (WLAN), a wide area network (WAN), a metropolitan area network (MAN), a portion of the Internet, or another network 421 or a combination of two or more such networks 150. The present disclosure contemplates any suitable network 150.

One or more links couple one or more systems, engines or devices to the network 150. In particular embodiments, one or more links each includes one or more wired, wireless, or optical links. In particular embodiments, one or more links each includes an intranet, an extranet, a VPN, a LAN, a WLAN, a WAN, a MAN, a portion of the Internet, or another link or a combination of two or more such links. The present disclosure contemplates any suitable links coupling one or more systems, engines or devices to the network 150.

In particular embodiments, each system or engine may be a unitary server or may be a distributed server spanning multiple computers or multiple datacenters. Systems, engines, or modules may be of various types, such as, for example and without limitation, web server, news server, mail server, message server, advertising server, file server, application server, exchange server, database server, or proxy server. In particular embodiments, each system, engine or module may include hardware, software, or embedded logic components or a combination of two or more such components for carrying out the appropriate functionalities implemented or supported by their respective servers. For example, a web server is generally capable of hosting websites containing web pages or particular elements of web pages. More specifically, a web server may host HTML files or other file types, or may dynamically create or constitute files upon a request, and communicate them to clients devices or other devices in response to HTTP or other requests from clients devices or other devices. A mail server is generally capable of providing electronic mail services to various clients devices or other devices. A database server is generally capable of providing an interface for managing data stored in one or more data stores.

In particular embodiments, one or more data storages may be communicatively linked to one or more servers via one or more links. In particular embodiments, data storages may be used to store various types of information. In particular embodiments, the information stored in data storages may be organized according to specific data structures. In particular embodiment, each data storage may be a relational database. Particular embodiments may provide interfaces that enable servers or clients to manage, e.g., retrieve, modify, add, or delete, the information stored in data storage.

The system may also contain other subsystems and databases, which are not illustrated in FIG. 1, but would be readily apparent to a person of ordinary skill in the art. For example, the system may include databases for storing data, storing features, storing outcomes, training sets, and storing models. Other databases and systems may be added or subtracted, as would be readily understood by a person of ordinary skill in the art, without departing from the scope of the invention.

Figure 2:
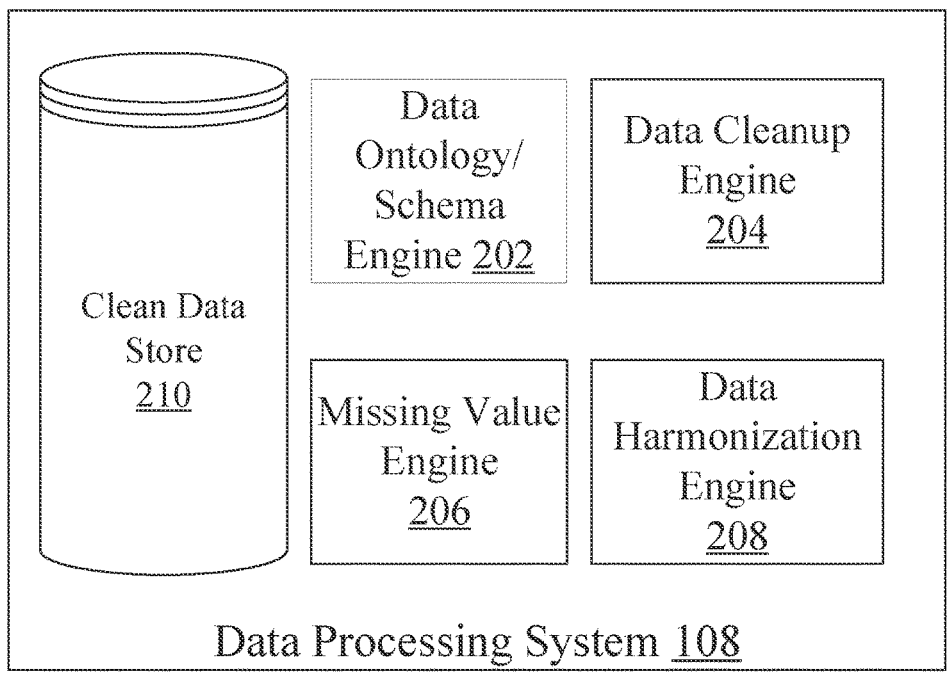
FIG. 2 illustrates an exemplary data processing system for the AI based training and recommendation system, in accordance with an embodiment of the invention.

FIG. 2 illustrates an exemplary implementation of the data processing system 108 in accordance with an embodiment of the invention. As described above, the data processing system 108 processes raw data. For example, the data processing system 108 may ingest data through dedicated APIS, store the data in a database for traceability purposes, organize the data according to the data ontology, cleanup the data (i.e. detect aberrant values and encoding of variables according to the ontology), perform missing value management and storage into the clean data bucket. More specifically the data processing system 108 is comprised of data ontology/schema engine 202, data cleanup engine 204, missing value engine 206, data harmonization engine 208, and clean data store 210. The various data modules and datastores may be implemented in Python using Jupyter notebooks in accordance with an embodiment of the invention. However, other implementation systems may be used, as would be apparent to a person of ordinary skill in the art without departing from the scope of the invention.

The data ontology/schema engine 202 organizes data. Ontologies can be pivotal tools for addressing the limitations of procedural systems such as autonomous agents. Ontologies are specifications of terms used in a particular domain and their relations to other terms. Examples of standard ontology languages include, but are not limited to XML, RDF and their extensions such as OWL and DAML+OIL. Potentially, ontologies provide: knowledge scalability (the ability to encode and manage very large knowledge bases), reuse of knowledge (across agents and possibly domains), increased robustness (agents can draw on ontological relationships to reason about novel or unanticipated events in the domain), and a foundation for interoperability among heterogeneous agents. These benefits together allow applications to be developed more quickly, maintained less expensively, and adapted to new tasks more readily. Ontology languages and tools focus on definitions and relationships more than the application of this knowledge in the execution of agent tasks. For information retrieval and web-based applications, the performance costs of using wholly declarative approaches may be acceptable. However, in performance environments, such as robotics and real-time simulation, agent responsiveness is an important requirement. In one embodiment, the data ontology/schema engine 202 establishes a data taxonomy to provide a unified view of the input data and introduces common terminologies and semantics across the multiple data sources. The taxonomy establishes a hierarchy within a set of metadata and segregates the data into different categories such as, for example, health data, life-style data, pharmacological treatments, non-pharmacological treatments, supplements, etc., to create a better understanding of the relationships between data points. In one embodiment, the data ontology/schema engine 202 also ensures that sensitive health data is processed in accordance with privacy and security standards.

The data cleanup engine 204 processes training data and/or other processed data for compliance with the established taxonomy. In one embodiment, the data that is cleaned by the cleanup engine 204 gets aggregated into a single repository following the predefined data taxonomy, annotated, and harmonized into a cohesive cloud database. A variety of different data cleanup techniques may be applied, as would be understood by a person of ordinary skill in the art, without departing from the scope of the invention.

The missing value engine 206 analyzes training data (and/or other data that may be processed by the modules described herein) for missing values. A variety of missing value computation systems may be applied, as would be apparent to a person of ordinary skill in the art, without departing from the scope of the invention, including, but not limited to using K-Nearest Neighbors (KNN) for variables that present an acceptable degree of missingness, which is typically less than 10% (but other measures of missingness may be used without departing from the scope of the invention.

The data harmonization engine 208 checks compliance of attributes/variables to their corresponding values in predefined formats. Aberrant values (such as a person allegedly weighing 1000 Kg) may be annotated for posterior manual assessment and fixing or just censored during the training phase. A variety of data harmonization techniques may be applied by the data harmonization engine 208, as would be apparent to a person of ordinary skill in the art, without departing from the scope of the invention.

The clean data store 210 stores the data from one or more of the processing engines 202, 204, 206, and 208. The clean data may be made available as input data for the data analysis and training system 110. The clean data store 210 may be embodied in a cloud system architecture and/or on premises servers, as would be apparent to a person of ordinary skill in the art.

Figure 3:
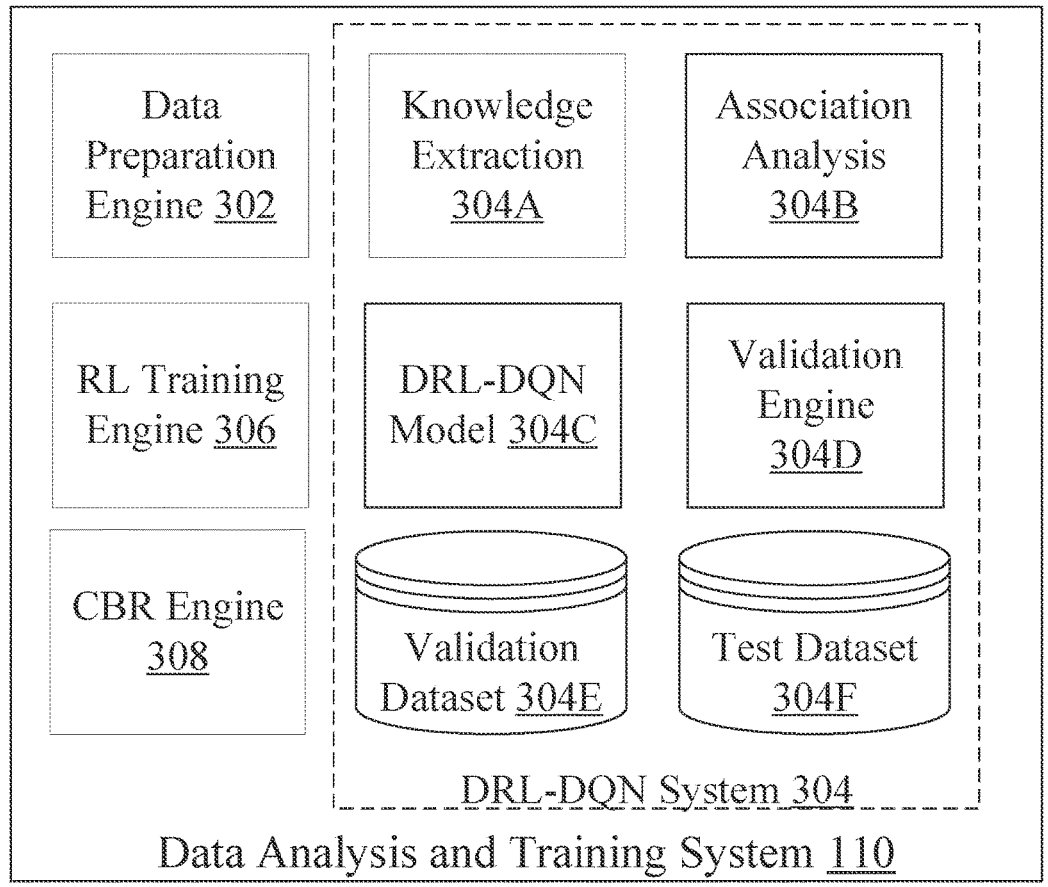
FIG. 3 illustrates an exemplary data analysis and training system for the AI based training and recommendation system, in accordance with an embodiment of the invention.

FIG. 3 illustrates the modular treatment recommendation system of the present invention. It may be comprised of a data preparation engine 302, a DRL-DQN system 304, RL training engine 306, and a CBR engine. Other systems and/or methods for performing the processes described herein may be used or applied as would be apparent to a person of ordinary skill in the art, without departing from the scope of the invention.

As mentioned above, and described below in more detail, a key innovative feature of presently described systems and methods is that it enables modular training by using two or more training/learning techniques. The various different models may be trained on the same set of underlying data and/or system architecture or implementations. Moreover, various training systems may be compared in real-time to enable real-time decisioning (or serve as a comparison to clinical models). In other instances, the various training systems may serve as fall back options in case of errors or null/void values.

The data preparation engine 302 prepares datastreams for analysis. In one embodiment, datastreams from the clean data store 210 may be processed by the data preparation engine 302. In some instances, data processing by the data preparation engine 302 may overlap with the processes executed by the data processing system 108. In other embodiments, the data processing systems and methods disclosed herein may be performed in one or both systems, the data progressing system 108 and/or the data preparation engine 302. Generally, the data preparation engine 302 may fill-in missing variable and/or values, may filter the data, standardize the data, and split the data into training data, validation data, test data, etc.

More specifically, in accordance with an embodiment of the invention, the data preparation engine 302 identifies missing values and imputates a value for them by applying a K-nearest neighbors (KNN) algorithm (other imputation techniques may be used without departing from the scope of the invention). In one embodiment, the data preparation engine 302 identifies variables that present an acceptable degree of missingness (for example, but not limited to, less than 10%). In an exemplary use case, (assuming that the data processing systems and methods disclosed herein were used to monitor estrogen levels (to potentially make recommendations regarding perimenopause). In those instances, the data model may be comprised of a variable named 'estrogen.' In, for example, a population of 3,000 women, there might be 250 cases where these values are missing. In this particular case, the data preparation engine 302 applies imputation techniques to fill these values from the data most similar to each single case through KNN. Thereafter, data may be further analyzed to filter variables that are equal to zero (to filter variables that do not convey any information). The data model may also be comprised of another variable termed 'sex,' which may be encoded as 1 for males and 2 for females. In this particular example of making recommendations for perimenopause, this variable would only have a value of 2 because our end users would be only women. Thus, the standard deviation of the 'sex' variable would be 0 and, thus, this variable would be censored from analysis. After that, the data may be standardized (e.g. z-score for numeric values or encoded for categorical variables) so that it could be analyzed efficiently.

In one embodiment, the data preparation engine 302 may split the datastream into training dataset, validation dataset 304E, and test dataset 304F. In the instances wherein the dataset or datastream is unbalanced (i.e. there is not a 50% proportion between positive and negative cases), the data preparation engine 302 splits the data in such a way, as would be understood by persons of ordinary skill in the art, that the balance between classes is kept among the various split datasets, such as the training dataset, validation dataset, test dataset, etc.

The DRL-DQN system 304 trains a DRL-DQN model. It may be comprised of a knowledge extraction engine 304A, an association analysis engine 304B, a DRL-DQN training engine 304C, a validation engine 304D, a validation dataset 304E, and a validation dataset 304F. However, other system architectures may be employed to accomplish the same functionality, as would be apparent to a person of ordinary skill in the art, without departing from the scope of the invention.

The knowledge extraction engine 304A ascertains patient phenotypes from data made available by the data preparation engine 302. In one embodiment, the knowledge extraction engine 304A ascertains patient phenotypes from relevant patient symptom and health data that is made available by the data preparation engine 302. In one embodiment, one or more phenotypes may be associated with one or more attributes (which may include for example, symptoms, treatments, etc.). A variety of different knowledge extraction methodologies may be used, as would be readily understood by a person of ordinary skill in the art, without departing from the scope of the invention.

In one embodiment, the knowledge extraction engine 304A ascertains phenotypes by applying an unsupervised consensus k-means clustering algorithm. In another embodiment, phenotypes may be identified by applying standard multivariate methods such as factor analysis. Generally, the ascertained phenotypes may subsume symptom data and/or variables. Referring back to the example of perimenopause, some of the symptoms may be mood changes or issues in regulating body temperature. Even though these symptoms may be generally present, they may affect different people differently. Thus, the knowledge extraction engine 304A may ascertain phenotypes related to 'mood changes' and another to 'body temperature,' which subsume all the data available for these two symptoms, for example. In other example, related to IBS, some of the risk factors may be: age, sex, family history, and mental health (i.e anxiety, depression or other issues). In that instance, the knowledge extraction engine 304A may ascertain patient phenotypes along these risk factors to summarize patient status and, also, identify the root symptoms and variables associated with them. The clinical/physiological relevance of the resulting phenotypes may be validated by receiving input from domain experts.

The association analysis engine 304B ascertains associations for the phenotypes identified by the knowledge extraction engine 304A. In one embodiment, the association analysis engine 304B may identify associations between the ascertained phenotypes based on correlation or mutual information between phenotypes and/or the attributes associated with phenotypes. In another embodiment, the association analysis engine 304B ascertains associations among phenotypes and/or available treatments. The association analysis engine 304B may also ascertain associations over time as a patient's symptoms evolve and/or as the patient responds to a given course of interventions. In this manner, the association analysis engine 304B ascertains associations over a threshold period time, which may be used to compute patient trajectories. With this approach, the association analysis engine 304B obtains an informative subset of data consisting of phenotypes (including their corresponding attributes) and the most informative treatments at a given point of time. A variety of different association analysis systems may be applied, as would be readily apparent to a person of ordinary skill in the art, without departing from the scope of the invention. For example, in one embodiment, the association analysis can be performed by applying a causal explorer package, which assesses mutual information between attributes for the association analysis.

Referring to the example above related to the IBS condition, the following description illustrates one exemplary embodiment of how the data extraction engine 304A and the association analysis engine 304B may process a variety of data. For example, if a patient with IBS has a family history of IBS (assuming the data reveals that the patient's mother reported IBS in the past and also there are two single nucleotide polymorphisms (SNPs) related to IBS from her genetic data). However, the data also provides that the patient reports a severe problem of anxiety, and the patient is following a psychotherapy treatment. Furthermore, the patient data reveals that the patient is highly stressed as shown by her heart-rate (HR) readings from a wearable device. Her blood pressure data also reveals that her blood pressure (BP) is also highly variable. The patient reports a lack of focus and concentration in the questionnaire administered, which is input during the data ingestion phase. Taking all these data into consideration, the data extraction engine 304A may assign the patient to the 'mental health' phenotype. After some time, assuming the data provides that the patient has followed a regime prescribed by the system of psychotherapy, and physical activity. (Assuming for example, that the protocol has been validated by her doctor and accepted by the user and adhered to it for three months). As a result of her adherence to the protocol, the patient has been discharged from psychotherapy, has taken up a new healthy diet and is training three times a week, which is identified as a positive 'trajectory' by the association analysis engine 304B. With this new state/identified trajectory, the patient can now be moved to the 'family history' phenotype as recommended by a recommendation engine (described in greater detail below), and start a maintenance regime, which may have been validated by a doctor and accepted by the patient.

The DRL-DQN training engine 304C trains a DRL-DQN model based on data made available by the data extraction engine 304A and the association analysis engine 304B. In one embodiment traditional DRL-DQN training methodologies, which use convolutional neural networks (CNNs) may be used. In other embodiments, a modified DRL-DQN training methodology is used, which is believed to be novel. Generally, the present invention is for using a stacked autoencoder (including, but not limited to variational autoencoders) with a DRL-DQN. The stacked/variational autoencoders enable the embedding of clinical knowledge and patient trajectories into a single patient signature, which may be used by the DRL and/or the recommendation engine (described in greater detail below).

A stacked autoencoder is a neural network that consists of several layers of sparse autoencoders where output of each hidden layer is connected to the input of the successive hidden layer. The hidden layers are trained by an unsupervised algorithm and then fine-tuned by a supervised method. Stacked autoencoder mainly consist of the following steps: (1) train autoencoder using input data and acquire the learned data, (2) the learned data from the previous layer is used as an input for the next layer and this continues until the training is completed, and (3) once all the hidden layers are trained use the backpropagation algorithm to minimize the cost function and weights are updated with the training set to achieve fine tuning. In a variational autoencoder, instead of mapping an input to fixed vector, input is mapped to a distribution. A difference between the autoencoder and variational autoencoder is that bottleneck vector is replaced with two different vectors one representing the mean of the distribution and the other representing the standard deviation of the distribution. An exemplary loss function for variational autoencoder is provided below:

$$li(\theta,\phi) = -Ez\sim q\theta(z|xi)[\log p\phi(xi|z)] + KL(q\theta(z|xi)\|p(z)$$

The loss function in variational autoencoder consists of two terms. First, one represents the reconstruction loss and the second term is a regularizer and KL means Kullback-Leibler divergence between the encoder's distribution $q\theta$ (z|x) and p (z). This divergence measures how much information is lost when using q to represent p. In other words, a variational autoencoder, like all autoencoders, is comprised of an encoder, a decoder, and a loss function, wherein the encoder is a neural net, the decoder is another neural net, and the loss function of the variational autoencoder is the negative log-likelihood with a regularizer. The regularizer may be a Kullback-Leibler divergence between the encoder's distribution, which measures how much information is lost (in units of nats) when using q to represent p. It is one measure of how close q is top. In the variational autoencoder, p is specified as a standard Normal distribution with mean zero and variance one. If the encoder outputs representations z that are different than those from a standard normal distribution, it will receive a penalty in the loss. This regularizer term means 'keep the representations z of each digit sufficiently diverse.' If the regulizer was not included, the encoder could learn to cheat and give each datapoint a representation in a different region of Euclidean space. The variational autoencoder is trained by the training engine 304C by using gradient descent (to optimize loss with respect to the parameters of the encoder and decoder) or stochastic gradient descent with variable step sizes.

Indeed, unlike CNNs, variational autoencoders summarize semantic information from various data sources. Moreover, the variational autoencoders enable the training engine 304C to assess the probability to transition to other states so that recommendations and interventions can be planned to maximize this transition probability to the most favorable state for the patient. The DRL-DQN training engine 304C may also update Q-values to assess patient progression through the computation of a set of indicators that measure the progress towards the intervention goal (including anomaly detection). Here, different outcomes may be defined such as symptoms remission, decrease of the number of exacerbations, number of unplanned visits to the doctor, number of ER visits or patient's self-perceived well-being. Since the outcomes can drive the accuracy of the recommendation engine (described in greater detail below), they may be defined in the beginning of the training phase and validated by domain experts.

In technical terms, the variational autoencoder of the modified DRL-DQN training engine 304C computes a state-space model. The state-space model may be obtained by computing the probability that a patient may be in a state based on the relative frequency in which the state is observed in the training dataset. Thereafter, the DRL-DQN training engine 304C computes an advantage of recommending a certain intervention a at a given state s A(s,a) as well as the value for this state as it is defined in standard DRL V(s) so that our Q-value is defined as Q(s,a)=A(s,a)+V(s) so that the DQN can be efficiently trained from the subset of data obtained from the knowledge extraction engine 304A, and the best course of action can be proposed from the Q-values obtained from a new patient entering the system without having to search over irrelevant training instances for the problem at hand.

The validation engine 304D validates the trained DRL-DQN model performance. As described above, the ingested data may be split into validation dataset 304E and test dataset 304F. The validation engine 304D applies data in the validation dataset 304E. The data in the validation dataset 304E is unseen by the training model, so the results from the validation engine 304D are useful to determine whether the newly trained DRL-DQN model will generalize to unseen data and/or provide actionable recommendations. The validation engine 304D may compute performance by measuring the error rate between proposed interventions and patient status. The validation engine 304D may further evaluate the trained DRL-DQN model performance by applying data from the test dataset 304F. If the results obtained during test are equivalent to the results obtained in the training and validation phases, the DQN shall be ready for deployment in a production environment with new data. A variety of different validation and/or testing techniques may be applied, which may be known to a person of ordinary skill in the art, without departing from the scope of the invention, including, but not limited to the McNemar statistical test.

In one embodiment, the training and validation processes can be re-run periodically and/or when a threshold amount of new data is made available.

The RL training engine 306 develops a Markov Decision Process (MDP) that could be used for training a reinforcement learning algorithm. RL training via a Markov decision process is known in the art. However, the data pipeline system, which allows parallel reinforcement learning via MDP and a DRL-DQN that is modified with variational autoencoders is believed to be novel. The specific aspects of the data pipeline that enables parallel processing is described in greater detail below. In some embodiments, the RL training engine 306 may run concurrently with the DRL-DQN system 304 and/or may run if the validation data produced by the validation engine 304D indicates that the DRL-DQN model is non-performant, is providing null/void values, and/or not providing meaningful.

The case-based reasoning (CBR) training engine 308 applies semi-supervised training to create a CBR training model. The CBR training model may be deployed to identify and recommend interventions to patients. Semi-supervised training may be performed by applying some labelled training data with unlabelled data. Generally, labeled data may represent clinically validated data comprising symptom data, outcome data, diagnosis data, intervention recommendation data, etc. In one embodiment, the labeled data may be obtained from a variety of sources, including, but not limited to, clinical data obtained from empirical sources, and/or from interventions that have been approved and/or validated by clinicians after an intervention is proposed by a recommendation engine. The data pipeline and architecture for enabling parallel processing for DRL-DQN model, RL model, and/or CBR training model is believed to be novel. The specific aspects of the data pipeline/architecture that enables parallel processing is described in greater detail below. In some embodiments, the CBR training engine 308 may run concurrently with the DRL-DQN system 304 and/or may run if the validation data produced by the validation engine 304D indicates that the DRL-DQN model is non-performant, is providing null/void values, and/or not providing meaningful. In one embodiment, the CBR training model 308 may be retrained if a new case is validated and deemed appropriate by being added to a knowledge database (KDB). This approach enables incremental learning in which the KDB of the system is updated iteratively from new and existing patients. It also allows reusing knowledge from previous cases for decision making about new patients. Moreover, it avoids the 'cold start machine learning problem,' when prior information has not been collected from patients, through the reuse of knowledge/experience of the clinicians, and reuses clinical feedback for other similar patients entering the system.

Once the recommendation system is ready and set up in production, when data from a new patient is available, it is processed to obtain phenotypes and associations that are then fed into the recommendation system to obtain a personalized protocol for this patient, as described in greater detail below. Once the protocol is ready, validated and accepted by the patient, the adherence to the protocol, symptoms, psychosocial metrics and quality of life metrics can be monitored. Thus, this new stream of data may be fed into the pipeline for updating the available datasets that shall be later used for upgrading or fine-tuning the recommendation engine. This approach also enables integration with a CBR training model 308.

As illustrated, and described herein in reference to FIG. 3, the training system of the present invention is modular and may enable a variety of different training systems (including, but not limited to, DRL-DQN training system, RL training system, and CBR training system) may be trained with the same datasets and/or the same data processing pipeline and/or the same system training system architecture. This modularity permits models for each long-term condition to be optimized and adapted to the evolution of each phenotype or patient as new data becomes available. The modularity also makes the models and infrastructure compatible with different repositories (public and private), thus enabling the integration of results coming from different clinical studies. The DRL-DQN training system may be preferred in some embodiments because it can provide meaningful information and online personalized adaptations of the different intervention plans, but it also preferably uses a refactoring of the DQN algorithm to adapt it to the recommendation problem and requires a large number of data examples for training. The second implementation of developing a Markov decision process for training a RL algorithm is useful for cases in which there is not enough data or the DRL-DQN model does not converge to provide a meaningful result. The third option uses CBR and allows the iterative creation of a KDB (Knowledge Database) from which the treatment recommendations are proposed by reusing pre-existing cases.

Figure 4:
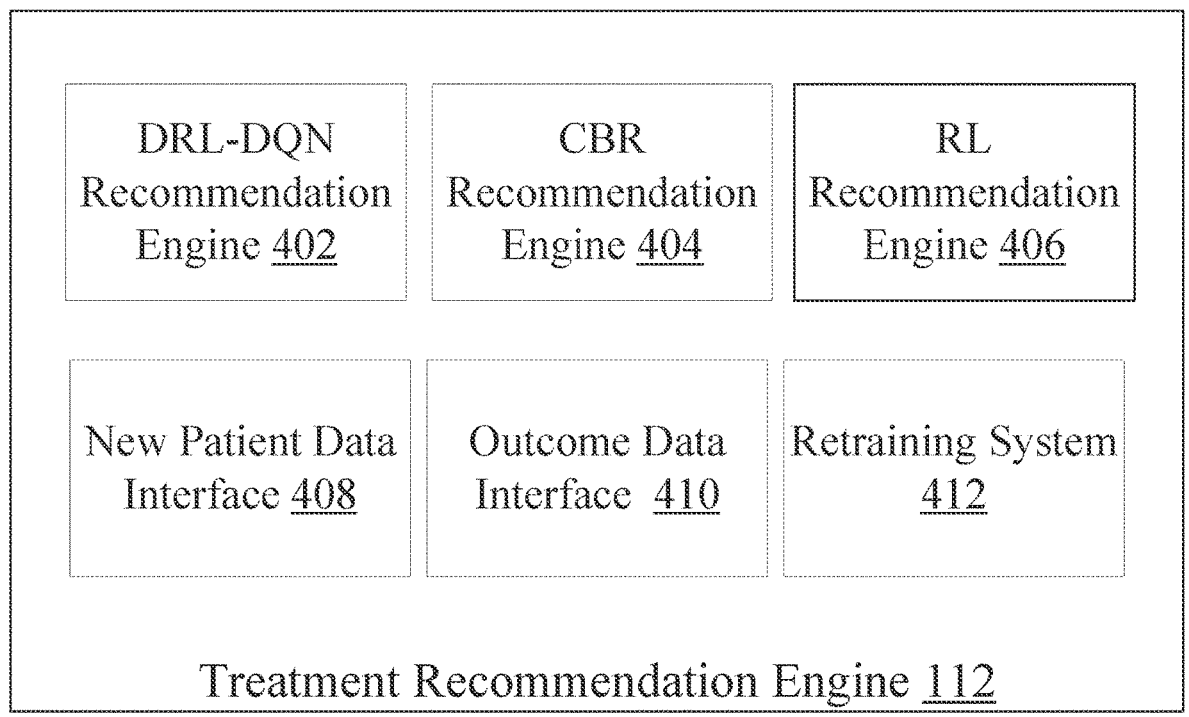
FIG. 4 illustrates an exemplary treatment recommendation engine for the AI based training and recommendation system, in accordance with an embodiment of the invention.

FIG. 4 illustrates a treatment recommendation engine 112 in accordance with an embodiment of the invention. The treatment recommendation engine 112 makes intervention recommendations based on trained models and incoming new patient data stream 102. It may be comprised of a DRL-DQN recommendation engine 402, a CBR recommendation engine 404, a RL recommendation engine 406, new patient data interface 408, outcome data interface 410, and retraining system 412. However, other systems and/or methodologies to perform the tasks described herein may be used, as would be understood by a person of ordinary skill in the art, without departing from the scope of the invention.

The DRL-DQN recommendation engine 402 provides treatment and/or intervention recommendations based on a model trained by the DRL-DQN training engine 304C and incoming, new patient data 102. More specifically, in accordance with an embodiment, the DRL-DQN recommendation engine 402 provides a course of action that is proposed from Q-values obtained from a new patient entering the system. In other words, when data from a new patient 102 is available, it is processed by the DRL-DQN recommendation engine 402 to obtain phenotypes and/or associations that are associated with the new patient data. The phenotypes and/or associations are then fed into the DRL-DQN recommendation engine 402 to obtain a personalized protocol for this patient based on Q-values obtained for the new patient data 102. This enables the DRL-DQN recommendation engine 402 to make recommendations without having to search over irrelevant training instances for the problem at hand. Once an intervention protocol is output by the DRL-DQN recommendation engine 402, it may be provided to a patient and/or a provider for validation and/or acceptance. From there, adherence data may be monitored, including, but not limited to symptom data, psychosocial metrics data, quality of life metrics, etc. As described in greater detail above and below, this new stream of data may be fed into the data analysis and training system 110 pipeline by the retraining system 412 to update the available datasets that may be later used for upgrading or fine-tuning the recommendation engine. This approach also enables an easy integration with a CBR methodology as described above.

The CBR recommendation engine 404 makes case based intervention recommendations. The CBR recommendation engine 404 essentially makes intervention recommendations by using previous data or memorized problem-solving situations/cases. In one embodiment, the CBR recommendation engine 404 initiates when a new case is entered into the system. The CBR recommendation engine 404 identifies N similar cases and retrieves them from a knowledge database for the comparison among all the cases in the system and this new case. The solutions adopted from the selected cases are reused and aggregated for this new case. In one embodiment, the proposed solution may be revised by a specialist based on input receive from an external system and/or device. If the solution is deemed appropriate by the CBR recommendation engine, it may be retained as a new case in the knowledge database (KDB).

More specifically, new patient data 102 may be obtained from, but not limited to, answers from baseline questionnaires, monitoring data, and so on). The CBR recommendation engine 404 may retrieve cases (i.e. user profiles) that are similar to this new patient data 102 from the knowledge database (KDB). This can be done through standard ML techniques such as k-NN, probabilistic clustering, and/or collaborative filtering. Indeed, a similarity function may be used to identify the user profiles, which are more similar to the new patient data 102. This function outputs a similarity score (SS) for each of the existing profiles in the KDB with respect to the current case. This score may be computed by a distance metric (e.g. euclidean, mahalanobis, hamming, and so on) among the values of the features that compose the existing case with the ones for the current patient multiplied by the importance of the features. Feature importance can also be assessed through other basic ML algorithms such as logistic regression, bayesian learners, random forests or even DRL. The output of this process by the CBR recommendation engine may be K profiles with the lowest distance. This distance can be converted to a probability score by normalizing it with respect to the maximum and minimum obtained distances. Once the patient profiles have been identified, the CBR recommendation engine 404 creates a plan by aggregating the actions from the selected cases, which have a support above the probability score (i.e. SO>SS). After that, the generated plan may be provided to a clinician who may prescribe the generated plan by adding/updating the set of actions to the intervention plan. After the clinician has updated the plan, the new case with the corresponding actions are stored in the KDB, and may be used by the retraining system 412, as described in greater detail below.

The RL recommendation engine 406 makes recommendations based on the reinforcement learning model developed in the data analysis and training system 110.

The new patient data interface 408 interfaces with computing devices that may provide new patient data 102. It may include, for example, systems for obtaining data from questionnaires, connected health devices, and others (as described elsewhere in the specification).

The outcome data interface 410 interfaces with computing devices to make intervention plan recommendations. For example, the outcome data interface 410 may send intervention plan recommendations to computing devices associated with a clinician and/or a patient. In other embodiments, the outcome data interface 410 may make the plan recommendation data available for others commuting devices to access and retrieve.

The retraining system 412 may interface with the data analysis and training system 110 to retrain the various model described herein based on new patient data 102 as well as clinician recommendation data, adherence data, and patient monitoring data.

Figure 5:
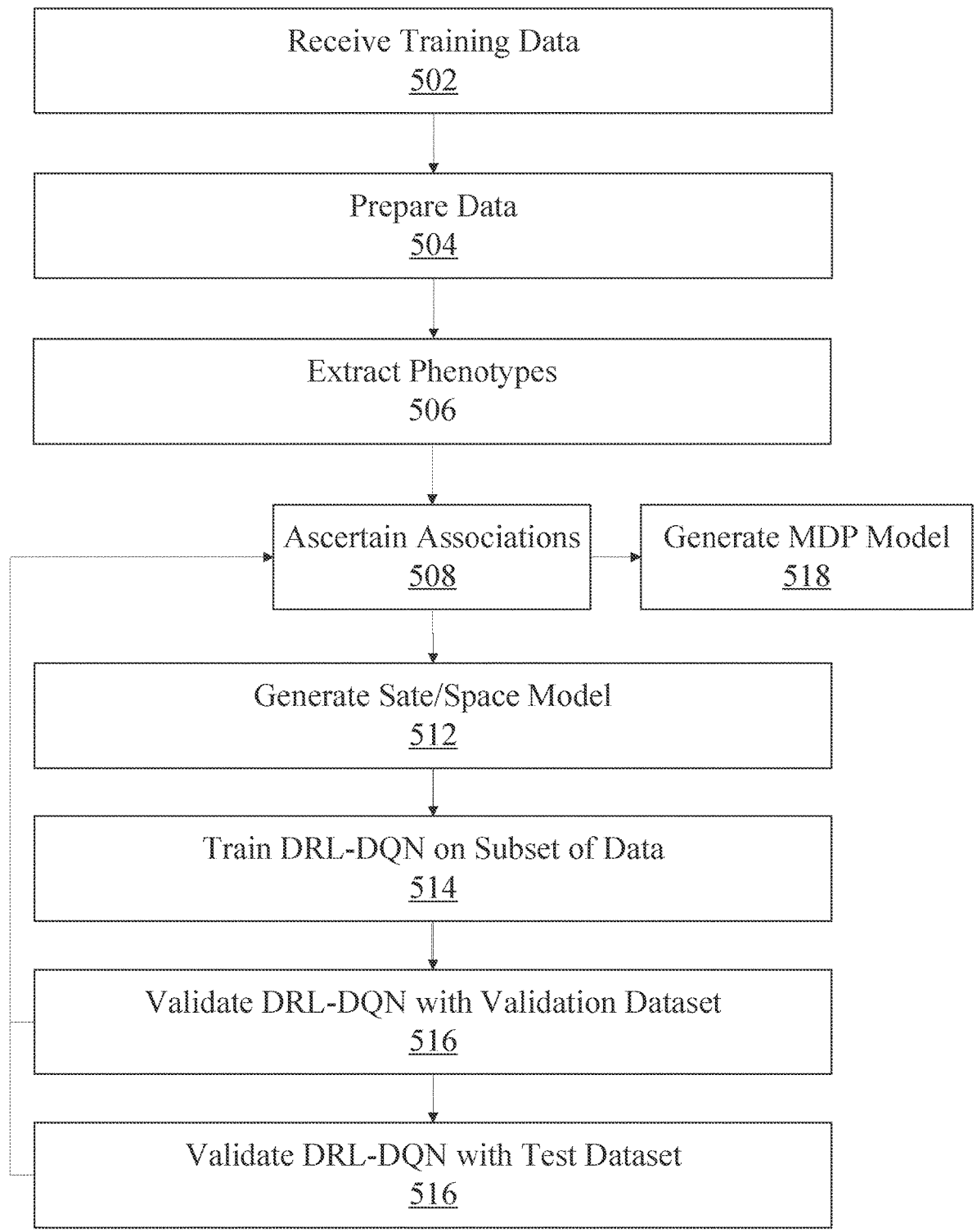
FIG. 5 illustrates an exemplary process for training a DRL-DQN and/or an RL model for the AI based training and recommendation system, in accordance with an embodiment of the invention.

FIG. 5 illustrates an exemplary process for managing a data pipeline to enable parallel processing of multiple ML based training models based on a same set of underlying data and processes.

The training process is described in greater detail in reference to FIG. 3. That disclosure is incorporated by reference herein.

The training process begins by receiving 502 training data. The training data may be prepared 504 by identifying missing values and imputing a value for the missing values by applying a K-nearest neighbors (KNN) algorithm (other imputation techniques may be used without departing from the scope of the invention). In one embodiment, variables that present an acceptable degree of missingness (for example, but not limited to, less than 10%) may be identified in the data preparation step 504. Thereafter, data may be further analyzed to filter variables that are equal to zero (to filter variables that do not convey any information). After that, the data may be standardized (e.g. z-score for numeric values or encoded for categorical variables) so that it could be analyzed efficiently. In addition, the data preparation step 504 may be comprised of splitting the datastream into training dataset, validation dataset and test dataset. In the instances wherein the dataset or datastream is unbalanced (i.e. there is not a 50% proportion between positive and negative cases), the data may be split in such a way, as would be understood by persons of ordinary skill in the art, that the balance between classes is kept among the various split datasets, such as the training dataset, validation dataset, test dataset, etc.

Phenotypes extraction step 508 may be comprised of ascertaining patient phenotypes from relevant patient symptom and health data. In one embodiment, one or more phenotypes may be associated with one or more attributes (which may include for example, symptoms, treatments, etc.). A variety of different knowledge extraction methodologies may be used, as would be readily understood by a person of ordinary skill in the art, without departing from the scope of the invention. In one embodiment, phenotypes may be ascertained by applying an unsupervised consensus k-means clustering algorithm. In another embodiment, phenotypes may be identified by applying standard multivariate methods such as factor analysis. Generally, the ascertained phenotypes may subsume symptom data and/or variables. The clinical/physiological relevance of the resulting phenotypes may be validated by receiving input from domain experts.

Association for phenotypes may be ascertained 508 at step 508. In one embodiment, associations between the ascertained phenotypes may be ascertained based on correlation or mutual information between phenotypes and/or the attributes associated with phenotypes. In another embodiment, association between phenotypes and/or available treatments may be ascertained. The association analysis may also be comprised of ascertaining associations over time as a patient's symptoms evolve and/or as the patient responds to a given course of interventions. In this manner, the associations may be ascertained over time, which may be used to compute patient trajectories. With this approach, an informative subset of data consisting of phenotypes (including their corresponding attributes) and the most informative treatments at a given point of time may be obtained. A variety of different association analysis systems may be applied, as would be readily apparent to a person of ordinary skill in the art, without departing from the scope of the invention. For example, in one embodiment, the association analysis can be performed by applying a causal explorer package, which assesses mutual information between attributes for the association analysis.

A state/space model may be generated at step 512. A variational autoencoder may be employed to compute a state-space model. The state-space model may be obtained by computing the probability that a patient may be in a state based on the relative frequency in which the state is observed in the training dataset. Thereafter, an advantage of recommending a certain intervention a at a given state s $A(s,a)$ as well as the value for this state as it is defined in standard DRL $V(s)$ may be computed so that the Q-value is defined as $Q(s,a)=A(s,a)+V(s)$. This permits the DQN to be efficiently trained from the subset of data obtained from the knowledge extraction step, and the best course of action can be proposed from the Q-values obtained from a new patient entering the system without having to search over irrelevant training instances for the problem at hand.

At step 516 and 518 the DRL-DQN may be trained 514 on a subset of data as described above (the training dataset and the test data set being generated at the data preparation step 504). The data in the validation dataset is unseen by the training model, so the results from the validation 516 are useful to determine whether the newly trained DRL-DQN model will generalize to unseen data and/or provide actionable recommendations. The validation may be performed by computing performance by measuring the error rate between proposed interventions and patient status. The DRL-DQN model performance may be further evaluated by applying data from the test dataset. If the results obtained during test are equivalent to the results obtained in the training and validation phases, the DQN shall be ready for deployment in a production environment with new data. A variety of different validation and/or testing techniques may be applied, which may be known to a person of ordinary skill in the art, without departing from the scope of the invention, including, but not limited to the McNemar statistical test.

Figure 7:
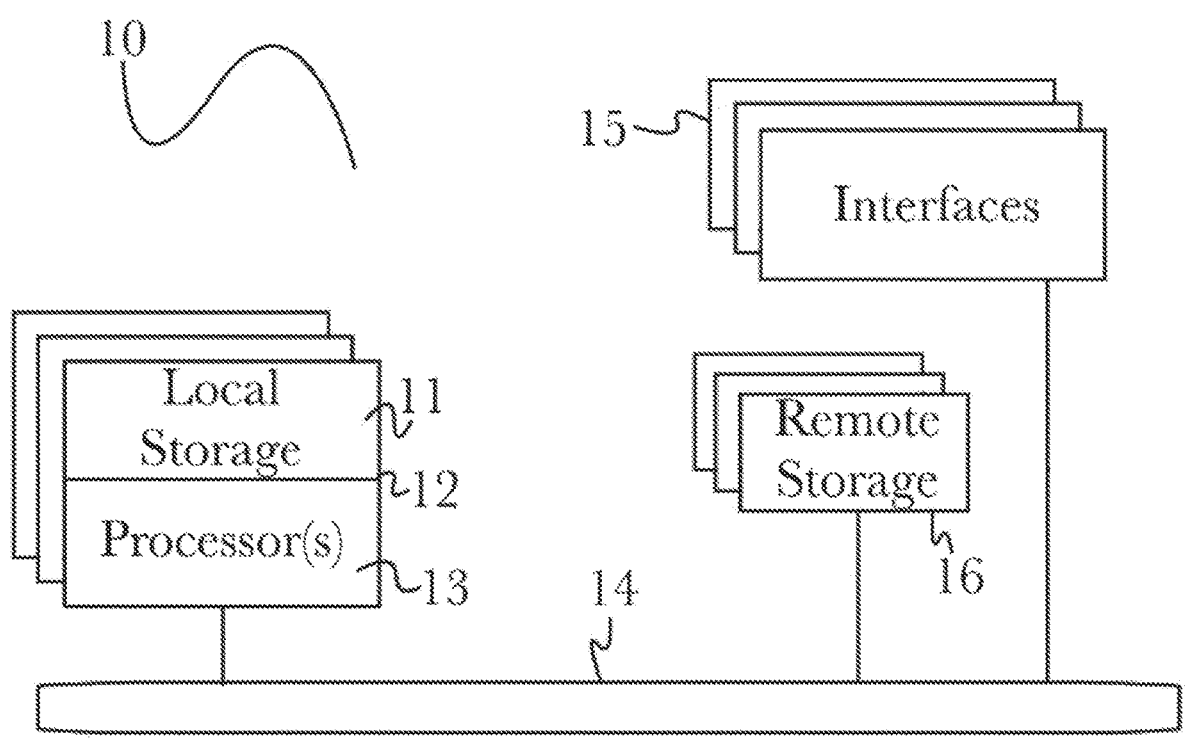
FIG. 7 illustrates one embodiment of the computing architecture that supports an embodiment of the inventive disclosure.

If the DRL-DQN fails validation or does not generalize— or, in one embodiment, regardless of the outcome of the validation steps 516 and/or 518, the process may skip to the ascertain association step 508 to generate an MDP model for RL learning. Reinforcement learning is particularly useful for the problem at hand because it can use an expanded set of complex data inputs including, numeric values, text, monitoring data and so on to recommend specific actions at sequential decision points. In particular, the agent learns to map states (patient conditions/symptoms) to actions that maximize a reward (clinical outcome). Actions affect both the immediate outcomes as well as all subsequent states. RL develops optimal value functions and decision-making policies in order to identify sequences of actions yielding the greatest probability of long-term favorable outcomes as conditions of uncertainty evolve over time. Interactions between a learning algorithm and its environment often occur within a Markov Decision Process containing states, actions, state-transition probabilities, and rewards as shown in FIG. 7

Figure 6:
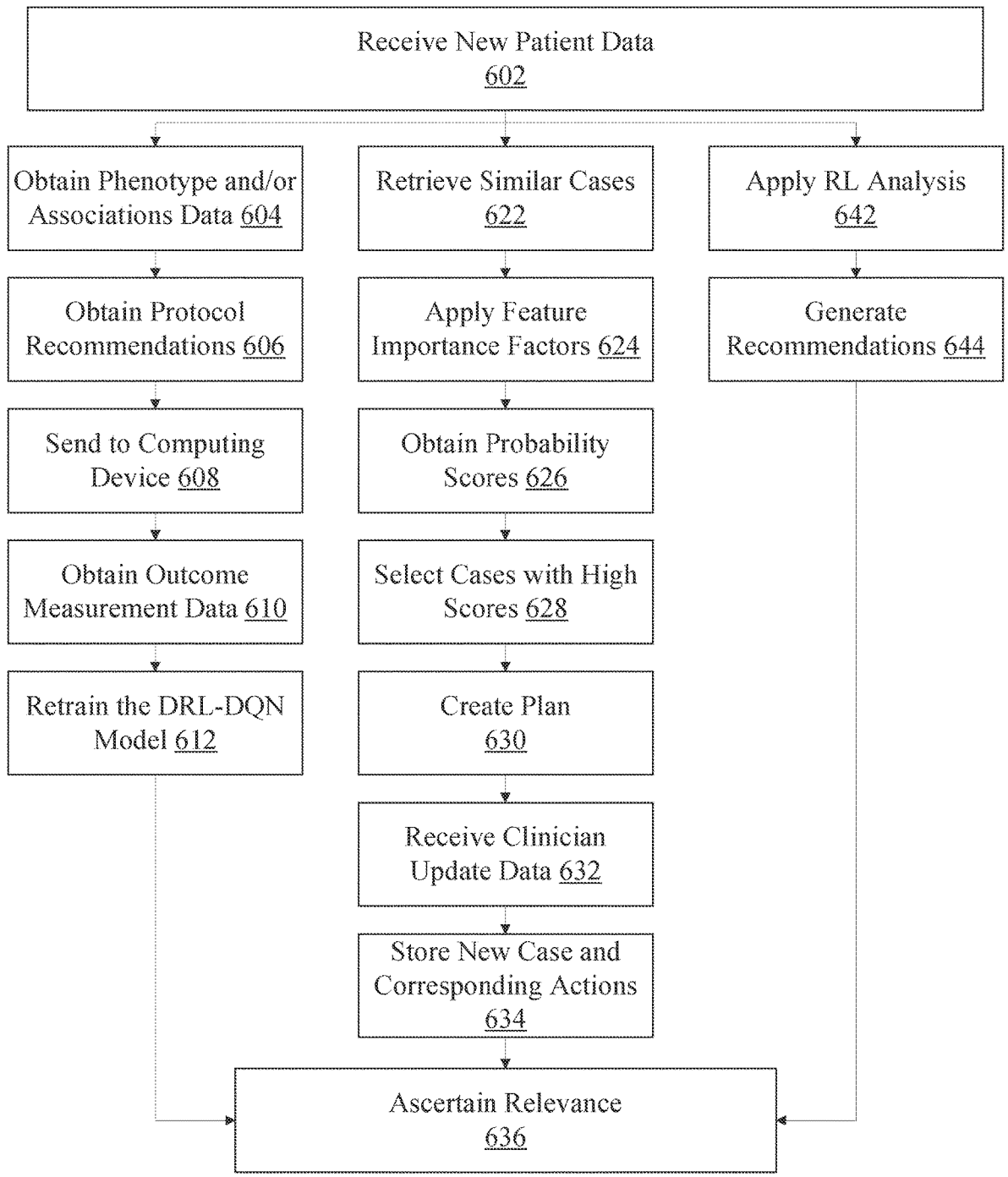
FIG. 6 illustrates an exemplary process for making intervention recommendations for the AI based training and recommendation system, in accordance with an embodiment of the invention.

FIG. 6 illustrates an exemplary process for making recommendations. This process enables efficient processing and includes interpretability measures for ascertaining relevance of recommendations proposed by various recommendation processes described herein. In particular, interpretability comes from a comparison between the recommendations made for a new case and those stored in a database of prior cases. This approach makes it possible to predict potential patient trajectories, and, thus, patient progress. Moreover, the phenotypes, trajectories, and recommendations can be compared with standard clinical practice, which may be validated by clinicians (who, may include, but not limited to, doctors, nurses, physiotherapists, psychologists, etc.). In addition, the process enables further monitoring of patient status and trajectories to provide real-time recommendations such that patient progress and well-being can be evaluated at a plurality of steps in the patient's health and recovery journey.

The process begins by receiving new patient data 602. The new patient data may be processed by one or more recommendation processes. In some instances, the new patient data 602 may be processed by the DRL-DQN recommendation process, the CBR recommendation process, and/or the RL recommendation process.

The method steps under the DRL-DQN recommendation process, comprising of steps 604, 606, 608, 610 and 612 are described in greater detail above in reference to FIG. 4. That disclosure is incorporated by reference herein. Generally, new patient data 602 may be processed to obtain phenotype and/or association data 604 associated with the new patient data 602. A variety of processes may be used to obtain phenotype and/or association data 604, as would be readily understood by a person of ordinary skill in the art, without departing from the scope of the invention, including, but not limited to using the training data.

One or more protocol recommendations 606 may be obtained based on the obtained 604 phenotype and/or association data. The protocol recommendation may be comprised of, and not limited to, cognitive behavioral therapy (CBT), mindfulness-based stress reduction techniques (MBSR), CBT for insomnia (CBT-I), hypnotherapy, nutritional supplements, dietary recommendations, lifestyle changes, non-hormonal medications (SSRIs), hormonal medications (HRT), and other pharmacological, and non-pharmacological treatments.

The obtained protocol recommendations may be sent 608 to a computing device associated with one or more clinicians. As described above, clinicians may include, but not limited to, doctors, nurses, physiotherapists, psychologists, etc. The clinician may validate the obtained protocol recommendations based on standard clinical practice and/or other guidelines. Based on this validation, the clinician may recommend a new protocol and/or may provide the protocol to a patient for implementation.

Once the protocol is implemented by a patient, new outcome measurement data 610 may be obtained. A variety of outcome measurement information may be obtained, including, but not limited to diagnosis and symptom data, physiologic data (heart-rate, blood pressure and tests— genetic or hormonal), wearable/sensor/smartphone data (e.g. (physical activity or sleep data) and multilevel data (i.e. data ranges from physiologic levels to life-style or psychology), etc. This new outcome measurement data 610 may be connected to outcomes including, but not limited to: single outcomes or combinations thereof may be considered: symptoms remission, decrease of the number of exacerbations, number of unplanned visits to the doctor, number of ER visits or patient's self-perceived well-being.

The outcome measurement data may be used to retrain 612 the DRL-DQN model. In one embodiment, factors that are considered relevant in the management of long-term conditions can be added; others that become irrelevant may be discarded. Hence, the models developed in the project for each condition can be optimized and adapted to the evolution of each phenotype (or patient) as new data becomes available.

The method steps associated with the CBR process pipeline, embodiment by elements 622, 624, 626, 630, 632, and 634 are described above in reference to the CBR recommendation engine 404 in FIG. 4. That discussion is incorporated by reference herein. Generally, once new patient data is received 602, the process retrieves 622 similar cases from a knowledge base. The solutions adopted from the selected cases are reused and aggregated for the newly received 602 patient data to obtain a proposed solution. The proposed solution may be reviewed and/or revised by a clinician, and, if the solution is appropriate, it is retained as a new case in the knowledge database.

When a new patient data is received 602 in the form of, for example, answers from baseline questionnaires, monitoring data, and so on, CBR process retrieves 622 similar cases (i.e. user profiles) from the knowledge database (KDB). This can be done through standard ML techniques such as k-NN, probabilistic clustering or even collaborative filtering. A similarity function may be used to identify the user profiles, which are more similar to the current patient and/or received 602 new patient data. This function outputs a similarity score (SS) for each of the existing profiles in the KDB with respect to the current case.

A feature importance factor 624 may be applied. Feature importance can also be assessed through other basic ML algorithms such as logistic regression, bayesian learners, random forests or even DRL. In one embodiment, the similarity score (SS) is may be calculated by computing a distance metric (e.g. euclidean, mahalanobis, hamming, and so on) among the values of the features that compose the existing case with the ones for the current patient multiplied by the importance of the features.

Probability scores may be obtained 626 thereafter. Generally, the output of the computation described in the previous paragraph results in identifying K profiles. The K profiles with the lowest distance may be identified, and the distance data associated with the profiles may be obtained. In one embodiment, the distance is converted to a probability score by normalizing it with respect to the maximum and minimum obtained distances.

A plan may be created 630 based on obtained identified patient profiles with high scores. Generally, the process creates 630 a plan by aggregating the actions from the selected cases, which have a support above the probability score (i.e. SO>SS).

Thereafter, clinician update data may be received 632, which may include new plans and/or a validation of the created plan. In other words, the clinician may prescribe the plan and/or may add or update actions within the plan and then prescribe it to a patient.

The process stores 634 the new case associated with received 602 new patient data and corresponding actions in the created plan and/or in an updated plan provided by a clinician in a database. The new data may be used to retrain the CBR recommendation system in accordance with the description above, which is incorporated by reference.

Under the RL recommendation process, which is comprised of elements 642 and 644, the process may include applying RL analysis 642 to the received 602 new patient data. RL develops optimal value functions and decision-making policies in order to identify sequences of actions yielding the greatest probability of long-term favorable outcomes as conditions of uncertainty evolve over time. Interactions between a learning algorithm and its environment often occur within a Markov Decision Process containing states, actions, state-transition probabilities, and rewards.

New intervention recommendations may be generated 644 based on this RL analysis.

Once all of the models provide a recommendation, the process may continue to ascertain 636 relevance. In one embodiment, the relevance may be ascertained 636 by comparing the recommendations made for new cases and those stored in a prior cases database. This approach makes it possible to predict potential patient trajectories and, thus, patient progress. Moreover, the phenotypes, trajectories and recommendations can be compared with standard clinical practice and validated by the prescriptors (doctors, nurses, physiotherapists, psychologists and so on).

Generally, the techniques disclosed herein may be implemented on hardware or a combination of software and hardware. For example, they may be implemented in an operating system kernel, in a separate user process, in a library package bound into network applications, on a specially constructed machine, on an application-specific integrated circuit (ASIC), or on a network interface card.

Software/hardware hybrid implementations of at least some of the embodiments disclosed herein may be implemented on a programmable network-resident machine (which should be understood to include intermittently connected network-aware machines) selectively activated or reconfigured by a computer program stored in memory. Such network devices may have multiple network interfaces that may be configured or designed to utilize different types of network communication protocols. A general architecture for some of these machines may be described herein in order to illustrate one or more exemplary means by which a given unit of functionality may be implemented. According to specific embodiments, at least some of the features or functionalities of the various embodiments disclosed herein may be implemented on one or more general-purpose computers associated with one or more networks, such as for example an end-user computer system, a client computer, a network server or other server system, a mobile computing device (e.g., tablet computing device, mobile phone, smartphone, laptop, or other appropriate computing device), a consumer electronic device, a music player, or any other suitable electronic device, router, switch, or other suitable device, or any combination thereof. In at least some embodiments, at least some of the features or functionalities of the various embodiments disclosed herein may be implemented in one or more virtualized computing environments (e.g., network computing clouds, virtual machines hosted on one or more physical computing machines, or other appropriate virtual environments).

Referring now to FIG. 7, there is shown a block diagram depicting an exemplary computing device 10 suitable for implementing at least a portion of the features or functionalities disclosed herein. Computing device 10 may be, for example, any one of the computing machines listed in the previous paragraph, or indeed any other electronic device capable of executing software- or hardware-based instructions according to one or more programs stored in memory. Computing device 10 may be configured to communicate with a plurality of other computing devices, such as clients or servers, over communications networks such as a wide area network a metropolitan area network, a local area network, a wireless network, the Internet, or any other network, using known protocols for such communication, whether wireless or wired.

In one aspect, computing device 10 includes one or more central processing units (CPU) 12, one or more interfaces 15, and one or more busses 14 (such as a peripheral component interconnect (PCI) bus). When acting under the control of appropriate software or firmware, CPU 12 may be responsible for implementing specific functions associated with the functions of a specifically configured computing device or machine. For example, in at least one aspect, a computing device 10 may be configured or designed to function as a server system utilizing CPU 12, local memory 11 and/or remote memory 16, and interface(s) 15. In at least one aspect, CPU 12 may be caused to perform one or more of the different types of functions and/or operations under the control of software modules or components, which for example, may include an operating system and any appropriate applications software, drivers, and the like.

CPU 12 may include one or more processors 13 such as, for example, a processor from one of the Intel, ARM, Qualcomm, and AMD families of microprocessors. In some embodiments, processors 13 may include specially designed hardware such as application-specific integrated circuits (ASICs), electrically erasable programmable read-only memories (EEPROMs), field-programmable gate arrays (FPGAs), and so forth, for controlling operations of computing device 10. In a particular aspect, a local memory 11

(such as non-volatile random-access memory (RAM) and/or read-only memory (ROM), including for example one or more levels of cached memory) may also form part of CPU 12. However, there are many different ways in which memory may be coupled to system 10. Memory 11 may be used for a variety of purposes such as, for example, caching and/or storing data, programming instructions, and the like. It should be further appreciated that CPU 12 may be one of a variety of system-on-a-chip (SOC) type hardware that may include additional hardware such as memory or graphics processing chips, such as a QUALCOMM SNAPDRAGON™ or SAMSUNG EXYNOS™ CPU as are becoming increasingly common in the art, such as for use in mobile devices or integrated devices.

As used herein, the term "processor" is not limited merely to those integrated circuits referred to in the art as a processor, a mobile processor, or a microprocessor, but broadly refers to a microcontroller, a microcomputer, a programmable logic controller, an application-specific integrated circuit, and any other programmable circuit.

In one aspect, interfaces 15 are provided as network interface cards (NICs). Generally, NICs control the sending and receiving of data packets over a computer network; other types of interfaces 15 may for example support other peripherals used with computing device 10. Among the interfaces that may be provided are Ethernet interfaces, frame relay interfaces, cable interfaces, DSL interfaces, token ring interfaces, graphics interfaces, and the like. In addition, various types of interfaces may be provided such as, for example, universal serial bus (USB), Serial, Ethernet, FIREWIRE™, THUNDERBOLT™, PCI, parallel, radio frequency (RF), BLUETOOTH™, near-field communications (e.g., using near-field magnetics), 802.11 (WiFi), frame relay, TCP/IP, ISDN, fast Ethernet interfaces, Gigabit Ethernet interfaces, Serial ATA (SATA) or external SATA (ESATA) interfaces, high-definition multimedia interface (HDMI), digital visual interface (DVI), analog or digital audio interfaces, asynchronous transfer mode (ATM) interfaces, high-speed serial interface (HSSI) interfaces, Point of Sale (POS) interfaces, fiber data distributed interfaces (FDDIs), and the like. Generally, such interfaces 15 may include physical ports appropriate for communication with appropriate media. In some cases, they may also include an independent processor (such as a dedicated audio or video processor, as is common in the art for high-fidelity A/V hardware interfaces) and, in some instances, volatile and/or non-volatile memory (e.g., RAM).

Although the system shown in FIG. 7 illustrates one specific architecture for a computing device 10 for implementing one or more of the embodiments described herein, it is by no means the only device architecture on which at least a portion of the features and techniques described herein may be implemented. For example, architectures having one or any number of processors 13 may be used, and such processors 13 may be present in a single device or distributed among any number of devices. In one aspect, single processor 13 handles communications as well as routing computations, while in other embodiments a separate dedicated communications processor may be provided. In various embodiments, different types of features or functionalities may be implemented in a system according to the aspect that includes a client device (such as a tablet device or smartphone running client software) and server systems (such as a server system described in more detail below).

Regardless of network device configuration, the system of an aspect may employ one or more memories or memory modules (such as, for example, remote memory block 16 and local memory 11) configured to store data, program instructions for the general-purpose network operations, or other information relating to the functionality of the embodiments described herein (or any combinations of the above). Program instructions may control execution of or comprise an operating system and/or one or more applications, for example. Memory 16 or memories 11, 16 may also be configured to store data structures, configuration data, encryption data, historical system operations information, or any other specific or generic non-program information described herein.

Because such information and program instructions may be employed to implement one or more systems or methods described herein, at least some network device embodiments may include nontransitory machine-readable storage media, which, for example, may be configured or designed to store program instructions, state information, and the like for performing various operations described herein. Examples of such nontransitory machine-readable storage media include, but are not limited to, magnetic media such as hard disks, floppy disks, and magnetic tape; optical media such as CD-ROM disks; magneto-optical media such as optical disks, and hardware devices that are specially configured to store and perform program instructions, such as read-only memory devices (ROM), flash memory (as is common in mobile devices and integrated systems), solid state drives (SSD) and "hybrid SSD" storage drives that may combine physical components of solid state and hard disk drives in a single hardware device (as are becoming increasingly common in the art with regard to personal computers), memristor memory, random access memory (RAM), and the like. It should be appreciated that such storage means may be integral and non-removable (such as RAM hardware modules that may be soldered onto a motherboard or otherwise integrated into an electronic device), or they may be removable such as swappable flash memory modules (such as "thumb drives" or other removable media designed for rapidly exchanging physical storage devices), "hot-swappable" hard disk drives or solid state drives, removable optical storage discs, or other such removable media, and that such integral and removable storage media may be utilized interchangeably. Examples of program instructions include both object code, such as may be produced by a compiler, machine code, such as may be produced by an assembler or a linker, byte code, such as may be generated by for example a JAVA™ compiler and may be executed using a Java virtual machine or equivalent, or files containing higher level code that may be executed by the computer using an interpreter (for example, scripts written in Python, Perl, Ruby, Groovy, or any other scripting language).

Figure 8:
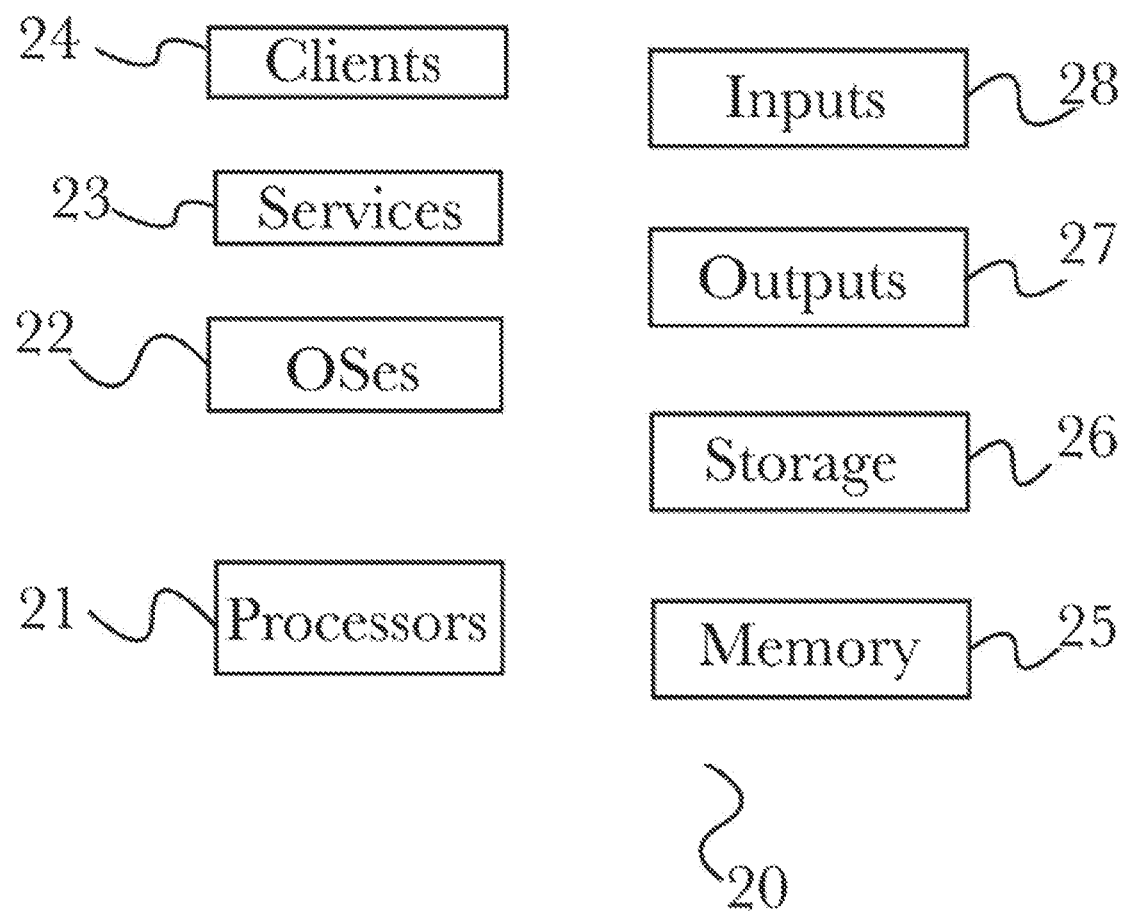
FIG. 8 illustrates components of a system architecture that supports an embodiment of the inventive disclosure.
Figure 9:
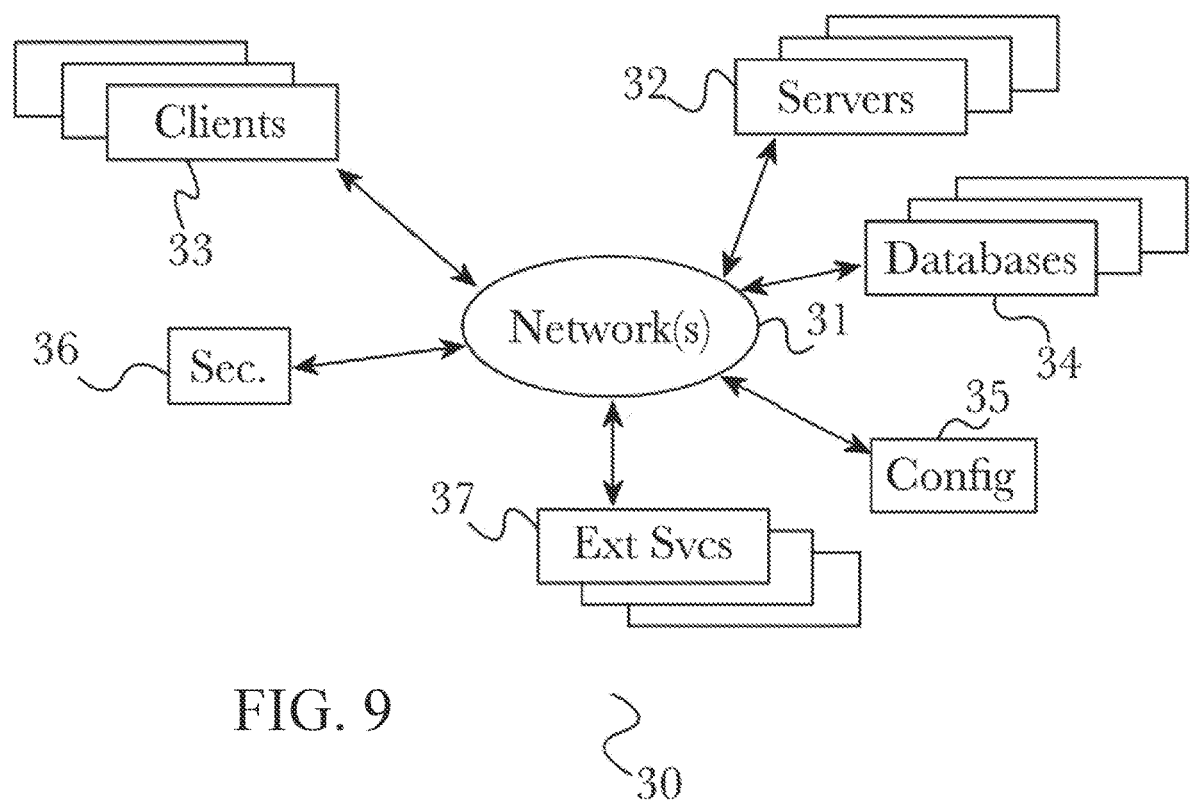
FIG. 9 illustrates components of a system architecture that supports an embodiment of the inventive disclosure.

In some embodiments, systems may be implemented on a standalone computing system. Referring now to FIG. 8, there is shown a block diagram depicting a typical exemplary architecture of one or more embodiments or components thereof on a standalone computing system. Computing device 20 includes processors 21 that may run software that carry out one or more functions or applications of embodiments, such as for example a client application 24. Processors 21 may carry out computing instructions under control of an operating system 22 such as, for example, a version of MICROSOFT WINDOWS™ operating system, APPLE macOS™ or iOS™ operating systems, some variety of the Linux operating system, ANDROID™ operating system, or the like. In many cases, one or more shared services 23 may be operable in system 20, and may be useful for providing common services to client applications 24. Services 23 may for example be WINDOWS™ services, user-space common services in a Linux environment, or any other type of common service architecture used with operating system 21. Input devices 28 may be of any type suitable for receiving user input, including for example a keyboard, touchscreen, microphone (for example, for voice input), mouse, touchpad, trackball, or any combination thereof. Output devices 27 may be of any type suitable for providing output to one or more users, whether remote or local to system 20, and may include for example one or more screens for visual output, speakers, printers, or any combination thereof. Memory 25 may be random-access memory having any structure and architecture known in the art, for use by processors 21, for example to run software. Storage devices 26 may be any magnetic, optical, mechanical, memristor, or electrical storage device for storage of data in digital form (such as those described above, referring to FIG. 4). Examples of storage devices 26 include flash memory, magnetic hard drive, CD-ROM, and/or the like In some embodiments, systems may be implemented on a distributed computing network, such as one having any number of clients and/or servers. Referring now to FIG. 9, there is shown a block diagram depicting an exemplary architecture 30 for implementing at least a portion of a system according to one aspect on a distributed computing network. According to the aspect, any number of clients 33 may be provided. Each client 33 may run software for implementing client-side portions of a system; clients may comprise a system 20 such as that illustrated in FIG. 9. In addition, any number of servers 32 may be provided for handling requests received from one or more clients 33. Clients 33 and servers 32 may communicate with one another via one or more electronic networks 31, which may be in various embodiments any of the Internet, a wide area network, a mobile telephony network (such as CDMA or GSM cellular networks), a wireless network (such as WiFi, WiMAX, LTE, and so forth), or a local area network (or indeed any network topology known in the art; the aspect does not prefer any one network topology over any other). Networks 31 may be implemented using any known network protocols, including for example wired and/or wireless protocols.

In addition, in some embodiments, servers 32 may call external services 37 when needed to obtain additional information, or to refer to additional data concerning a particular call. Communications with external services 37 may take place, for example, via one or more networks 31. In various embodiments, external services 37 may comprise web-enabled services or functionality related to or installed on the hardware device itself. For example, in one aspect where client applications 24 are implemented on a smartphone or other electronic device, client applications 24 may obtain information stored in a server system 32 in the cloud or on an external service 37 deployed on one or more of a particular enterprise's or user's premises.

In some embodiments, clients 33 or servers 32 (or both) may make use of one or more specialized services or appliances that may be deployed locally or remotely across one or more networks 31. For example, one or more databases 34 may be used or referred to by one or more embodiments. It should be understood by one having ordinary skill in the art that databases 34 may be arranged in a wide variety of architectures and using a wide variety of data access and manipulation means. For example, in various embodiments one or more databases 34 may comprise a relational database system using a structured query language (SQL), while others may comprise an alternative data storage technology such as those referred to in the art as "NoSQL" (for example, HADOOP CASSANDRA™, GOOGLE BIGTABLE™, and so forth). In some embodiments, variant database architectures such as column-oriented databases, in-memory databases, clustered databases, distributed databases, or even flat file data repositories may be used according to the aspect. It will be appreciated by one having ordinary skill in the art that any combination of known or future database technologies may be used as appropriate, unless a specific database technology or a specific arrangement of components is specified for a particular aspect described herein. Moreover, it should be appreciated that the term "database" as used herein may refer to a physical database machine, a cluster of machines acting as a single database system, or a logical database within an overall database management system. Unless a specific meaning is specified for a given use of the term "database", it should be construed to mean any of these senses of the word, all of which are understood as a plain meaning of the term "database" by those having ordinary skill in the art.

Figure 10:
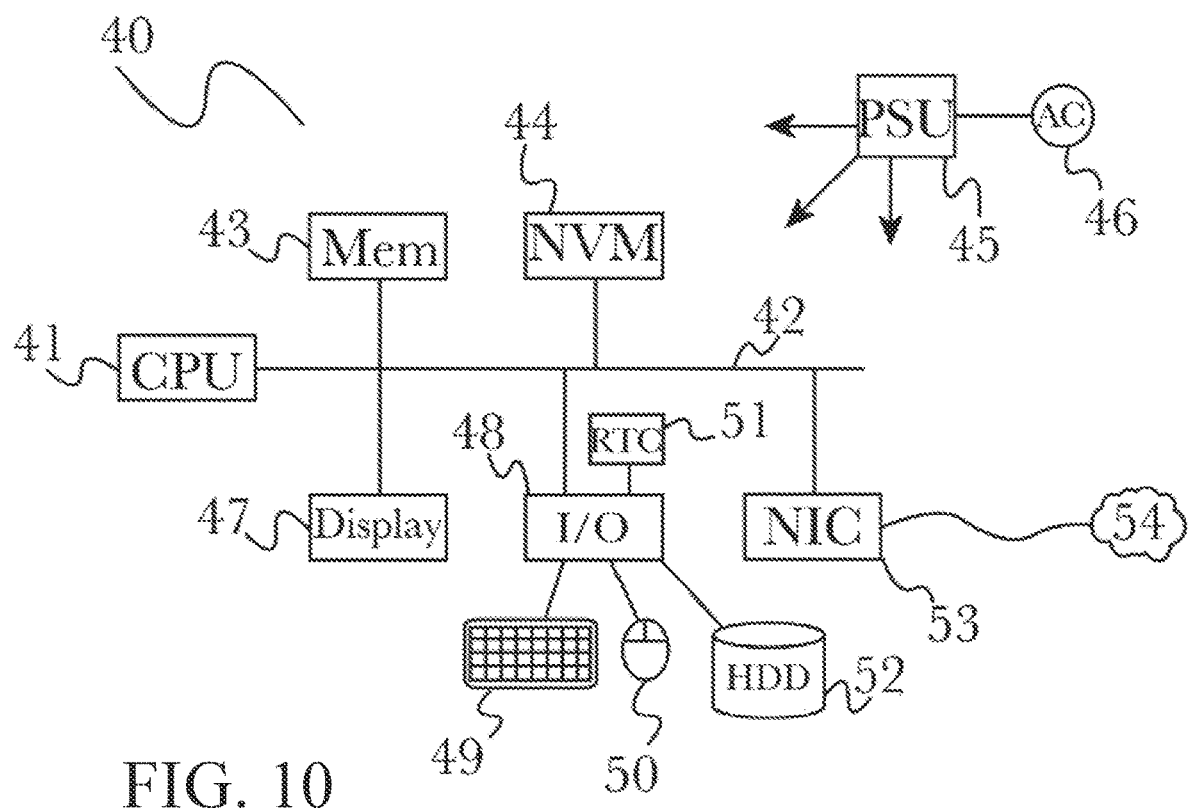
FIG. 10 illustrates components of a computing device that supports an embodiment of the inventive disclosure.

Similarly, some embodiments may make use of one or more security systems 36 and configuration systems 35. Security and configuration management are common information technology (IT) and web functions, and some amount of each are generally associated with any IT or web systems. It should be understood by one having ordinary skill in the art that any configuration or security subsystems known in the art now or in the future may be used in conjunction with embodiments without limitation, unless a specific security 36 or configuration system 35 or approach is specifically required by the description of any specific aspect FIG. 10 shows an exemplary overview of a computer system 40 as may be used in any of the various locations throughout the system. It is exemplary of any computer that may execute code to process data. Various modifications and changes may be made to computer system 40 without departing from the broader scope of the system and method disclosed herein. Central processor unit (CPU) 41 is connected to bus 42, to which bus is also connected memory 43, nonvolatile memory 44, display 47, input/output (I/O) unit 48, and network interface card (NIC) 53. I/O unit 48 may, typically, be connected to keyboard 49, pointing device 50, hard disk 52, and real-time clock 51. NIC 53 connects to network 54, which may be the Internet or a local network, which local network may or may not have connections to the Internet. Also shown as part of system 40 is power supply unit 45 connected, in this example, to a main alternating current (AC) supply 46. Not shown are batteries that could be present, and many other devices and modifications that are well known but are not applicable to the specific novel functions of the current system and method disclosed herein. It should be appreciated that some or all components illustrated may be combined, such as in various integrated applications, for example Qualcomm or Samsung system-on-a-chip (SOC) devices, or whenever it may be appropriate to combine multiple capabilities or functions into a single hardware device (for instance, in mobile devices such as smartphones, video game consoles, in-vehicle computer systems such as navigation or multimedia systems in automobiles, or other integrated hardware devices).

In various embodiments, functionality for implementing systems or methods of various embodiments may be distributed among any number of client and/or server components. For example, various software modules may be implemented for performing various functions in connection with the system of any particular aspect, and such modules may be variously implemented to run on server and/or client components.

The skilled person will be aware of a range of possible modifications of the various embodiments described above. Accordingly, the present invention is defined by the claims and their equivalents.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a system and a process for creating an interactive message through the disclosed principles herein. Thus, while particular embodiments and applications have been illustrated and described, it is to be understood that the disclosed embodiments are not limited to the precise construction and components disclosed herein. Various apparent modifications, changes and variations may be made in the arrangement, operation and details of the method and apparatus disclosed herein without departing from the spirit and scope defined in the appended claims.

What is claimed is:

1. A computer-implemented modular data system for processing multimodal data and enabling parallel model recommendations, the system comprising:
   one or more computers;
   and one or more computer memory devices interoperably coupled with the one or more computers and comprising tangible, non-transitory, machine-readable media storing one or more instructions that, when executed by the one or more computers, perform one or more operations comprising:
     ingesting data streams from a plurality of data sources;
     segmenting the ingested data stream into two or more of patient data, diagnosis data, symptom data, treatment data, patient reported data, and outcome data to obtain segmented data, wherein at least a portion of the segmented data is multimodal data;
     extracting phenotypes from the segmented data, the extracted phenotypes comprising one or more attributes;
     computing associations among two or more of the extracted phenotypes, the one or more attributes, and the treatment data over a threshold period of time to obtain computed association data;
     training a plurality of machine learned models based on the extracted phenotypes and/or the computed association data, each of the plurality of trained machine learned models comprising a reinforcement learning ("RL") technique, and a deep reinforcement learning with a dueling network architecture ("DRL-DQN") technique, the DRL-DQN technique being trained by applying variational autoencoders, and the RL technique producing a Markov Decision Process model;
     receiving new patient data;
     applying the plurality of trained machine learned models to the new patient data; and
     generating at least one treatment recommendation for one or more patients based on the applying.

2. The computer-implemented system of claim 1, wherein the DRL-DQN technique is trained on a subset of the segmented data, the subset of the segmented data being associated with the extracted phenotypes and the computed association data.

3. The computer-implemented system of claim 1, further comprising validating the DRL-DQN technique with validation data, the validation data being comprised of a portion of the ingested data streams.

4. The computer-implemented system of claim 3, further comprising validating the DRL-DQN technique with test data, the test data being comprised of a portion of the ingested data streams.

5. The computer-implemented system of claim 1, further comprising training a case-based-reasoning model based on the ingested data streams and empirical clinical data.

6. The computer-implemented system of claim 1, wherein the computing associations is comprised of applying statistical analysis to the extracted phenotypes and the treatment data over the threshold period of time to identify at least one patient trajectory for each extracted phenotype, the at least one identified patient trajectory identifying informative treatment options when a patient is assigned to at least one of the extracted phenotypes.

7. The computer-implemented system of claim 1, wherein the new patient data is comprised of at least one of multimodal data, physiologic data, computing device data, and multilevel data.

8. The computer-implemented system of claim 1, wherein the patient data is further comprised of at least one of patient health data, patient life-style data, patient medical history data, and patient genetic history data.

9. The computer-implemented system of claim 1, wherein the treatment data is further comprised of at least one of pharmacological treatment data, and non-pharmacological treatment data.

10. The computer-implemented system of claim 1, wherein the diagnosis data and/or symptom data is comprised of multimodal data comprising text.

11. The computer-implemented system of claim 1, wherein the patient reported data is comprised of data that is provided by a patient comprising at least one of food data, supplement data, and exercise data.

12. The computer-implemented system of claim 1, wherein the DRL-DQN technique generates a state-space model of the extracted phenotypes, wherein an advantage A(s,a) is defined of recommending a certain treatment a at a given state s of a phenotype using a Q-value Q(s,a)=A(s, a)+V(s), wherein A(s,a) comprises an advantage function defining a relative benefit of choosing a certain action a in state s over other possible actions in state s, and V(s) comprises a value function defining a relative benefit of being in state s, independent of relative benefits of actions in that state s, and wherein the at least one generated treatment recommendation is proposed by calculating a Q-value Q(s,a) from the new patient data and comparing the calculated Q-value with Q-values associated with the extracted phenotypes.

13. The computer-implemented system of claim 12, wherein the Q-value function provides a measure by which a convolution neural network of the DRL-DQN technique is trained.

14. The computer-implemented system of claim 13, wherein the Q-value function provides a measure by which at least one of the variational autoencoders is used to train the DRL-DQN technique.

15. The computer-implemented system of claim 1, wherein the extracting phenotypes is comprised of applying an unsupervised consensus k-means clustering algorithm to the segmented data.

16. The computer-implemented system of claim 15, wherein the extracting phenotypes is comprised of applying a standard multivariate factor analysis algorithm to the segmented data.

17. A computer-implemented method for creating a modular data system for processing multimodal data and enabling parallel machine learned model recommendations, the method comprising:
   ingesting data streams from a plurality of data sources;
   segmenting the ingested data stream into two or more of patient data, diagnosis data, symptom data, treatment data, patient reported data, and outcome data to obtain segmented data, wherein at least a portion of the segmented data is multimodal data;
   extracting phenotypes from the segmented data, the extracted phenotypes comprising one or more attributes;
   computing associations among two or more of the extracted phenotypes, the one or more attributes, and the treatment data over a threshold period of time to obtain computed association data;
   training a plurality of machine learned models based on the extracted phenotypes and/or the computed association data, each of the plurality of trained machine learned models comprising a reinforcement learning ("RL") technique, and a deep reinforcement learning with a dueling network architecture ("DRL-DQN") technique, the DRL-DQN technique being trained by applying variational autoencoders, and the RL technique producing a Markov Decision Process model;
   receiving new patient data;
   applying the plurality of trained machine learned models to the new patient data; and
   generating at least one treatment recommendation for one or more patients based on the applying.

18. A non-transitory, computer-readable medium storing one or more instruction executable by a computer system to perform operations for creating a modular data system for processing multimodal data and enabling parallel machine learned model recommendations, the operations comprising:
   ingesting data streams from a plurality of data sources;
   segmenting the ingested data stream into two or more of patient data, diagnosis data, symptom data, treatment data, patient reported data, and outcome data to obtain segmented data, wherein at least a portion of the segmented data is multimodal data;
   extracting phenotypes from the segmented data, the extracted phenotypes comprising one or more attributes;
   computing associations among two or more of the extracted phenotypes, the one or more attributes, and the treatment data over a threshold period of time to obtain computed association data;
   training a plurality of machine learned models based on the extracted phenotypes and/or the computed association data, each of the plurality of trained machine learned models comprising a reinforcement learning ("RL") technique, and a deep reinforcement learning with a dueling network architecture ("DRL-DQN") technique, the DRL-DQN technique being trained by applying variational autoencoders, and the RL technique producing a Markov Decision Process model;
   receiving new patient data;
   applying the plurality of trained machine learned models to the new patient data; and
   generating at least one treatment recommendation for one or more patients based on the applying.

* * * * *